(12) United States Patent
Bui et al.

(10) Patent No.: US 9,128,051 B2
(45) Date of Patent: Sep. 8, 2015

(54) OPTICAL IMAGING SYSTEM FOR AIR BUBBLE AND EMPTY BAG DETECTION IN AN INFUSION TUBE

(71) Applicants: Baxter International Inc., Deerfield, IL (US); Baxter Healthcare S.A., Glattpark (Opfikon) (CH)

(72) Inventors: Tuan Bui, Buffalo, NY (US); James F. Munro, Ontario, NY (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

(21) Appl. No.: 13/826,708

(22) Filed: Mar. 14, 2013

(65) Prior Publication Data
US 2013/0201471 A1  Aug. 8, 2013

Related U.S. Application Data

(63) Continuation-in-part of application No. 12/907,403, filed on Oct. 19, 2010, now Pat. No. 8,622,979.

(51) Int. Cl.
*G01N 21/00* (2006.01)
*G01N 21/59* (2006.01)

(52) U.S. Cl.
CPC ..................... *G01N 21/59* (2013.01)

(58) Field of Classification Search
CPC ..................................................... G01N 21/59
USPC .............. 604/65, 253, 131, 251, 122; 356/73
See application file for complete search history.

(56) References Cited

U.S. PATENT DOCUMENTS

| | | |
|---|---|---|
| 3,609,379 A | 9/1971 | Hildebrandt |
| 4,321,461 A | 3/1982 | Walter, Jr. et al. |
| 4,328,801 A | 5/1982 | Marx et al. |
| 4,504,263 A | 3/1985 | Steuer et al. |
| 4,525,163 A | 6/1985 | Slavik et al. |
| 4,583,975 A | 4/1986 | Pekkarinen et al. |
| 4,634,426 A | 1/1987 | Kamen |
| 4,673,820 A | 6/1987 | Kamen |
| 4,680,977 A | 7/1987 | Conero et al. |
| 4,703,314 A | 10/1987 | Spani |
| 4,718,896 A | 1/1988 | Arndt et al. |

(Continued)

FOREIGN PATENT DOCUMENTS

| | | |
|---|---|---|
| DE | 3617723 | 12/1987 |
| JP | 08305852 A | * 11/1996 |

(Continued)

*Primary Examiner* — Edelmira Bosques
(74) *Attorney, Agent, or Firm* — Greer, Burns & Crain Ltd.

(57) ABSTRACT

An optical imaging system for use with an infusion tube having a drip chamber and an output tube. The drip chamber includes a first portion with a drip tube, a second portion with an exit port, and a third portion between the first and second portions. The optical imaging system includes: an illumination system with at least one light source for emitting light, an optical system, and a memory element storing computer executable instructions. The optical system receives the light transmitted by the output tube or the second portion and transmits data characterizing the received light. The system includes at least one processor configured to execute the computer executable instructions to: detect, using the data, an air bubble in the output tube or the second portion; and determine a volume of the detected air bubble.

26 Claims, 19 Drawing Sheets

(56) References Cited

U.S. PATENT DOCUMENTS

| | | | |
|---|---|---|---|
| 4,820,281 | A | 4/1989 | Lawler, Jr. |
| 4,909,786 | A | 3/1990 | Gijselhart et al. |
| 4,936,828 | A | 6/1990 | Chiang |
| 5,045,069 | A | 9/1991 | Imparato |
| 5,057,090 | A | 10/1991 | Bessman |
| 5,186,057 | A | 2/1993 | Everhart |
| 5,267,980 | A | 12/1993 | Dirr, Jr. et al. |
| 5,331,309 | A | 7/1994 | Sakai |
| 5,415,641 | A | 5/1995 | Yerlikaya et al. |
| 5,479,816 | A * | 1/1996 | Richou et al. ............... 73/64.48 |
| 5,562,615 | A | 10/1996 | Nassif |
| 5,588,963 | A | 12/1996 | Roelofs |
| 5,899,665 | A | 5/1999 | Makino et al. |
| 6,049,381 | A | 4/2000 | Reintjes et al. |
| 6,083,206 | A | 7/2000 | Molko |
| 6,149,631 | A | 11/2000 | Haydel, Jr. |
| 6,159,186 | A | 12/2000 | Wickham et al. |
| 6,213,354 | B1 | 4/2001 | Kay |
| 6,562,012 | B1 | 5/2003 | Brown et al. |
| 6,599,282 | B2 | 7/2003 | Burko |
| 6,736,801 | B1 | 5/2004 | Gallagher |
| 6,974,435 | B2 * | 12/2005 | Daw et al. ............... 604/6.14 |
| 6,984,052 | B1 | 1/2006 | Del Castillo |
| 7,190,275 | B2 | 3/2007 | Goldberg et al. |
| 7,695,448 | B2 | 4/2010 | Cassidy et al. |
| 7,767,991 | B2 | 8/2010 | Sacchetti |
| 7,892,204 | B2 | 2/2011 | Kraus |
| 7,918,834 | B2 | 4/2011 | Mernoe et al. |
| 2003/0045840 | A1 | 3/2003 | Burko |
| 2006/0291211 | A1 | 12/2006 | Rodriguez et al. |
| 2008/0004574 | A1 | 1/2008 | Dyar et al. |
| 2008/0051732 | A1 | 2/2008 | Chen |
| 2010/0309005 | A1 | 12/2010 | Warner et al. |
| 2012/0013735 | A1 | 1/2012 | Tao |

FOREIGN PATENT DOCUMENTS

| | | |
|---|---|---|
| WO | 9309407 | 5/1993 |
| WO | 02/40084 | 5/2002 |
| WO | 2009039203 | 3/2009 |

* cited by examiner

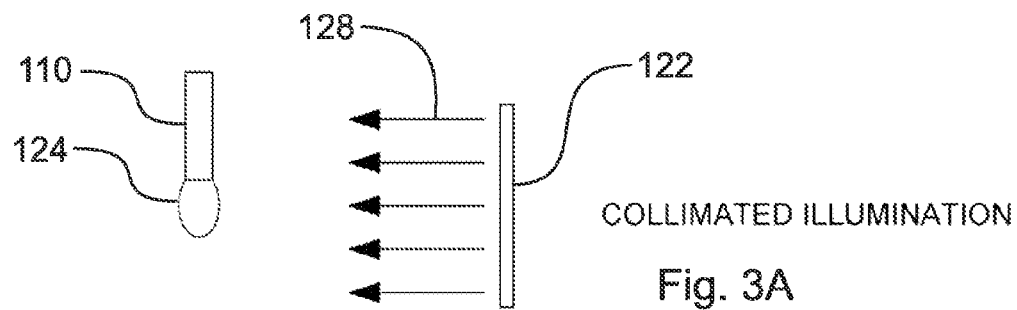
Fig. 3A COLLIMATED ILLUMINATION
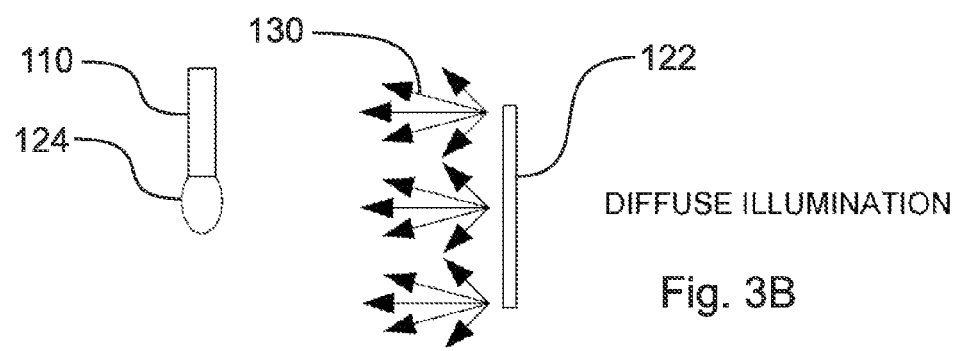
Fig. 3B DIFFUSE ILLUMINATION
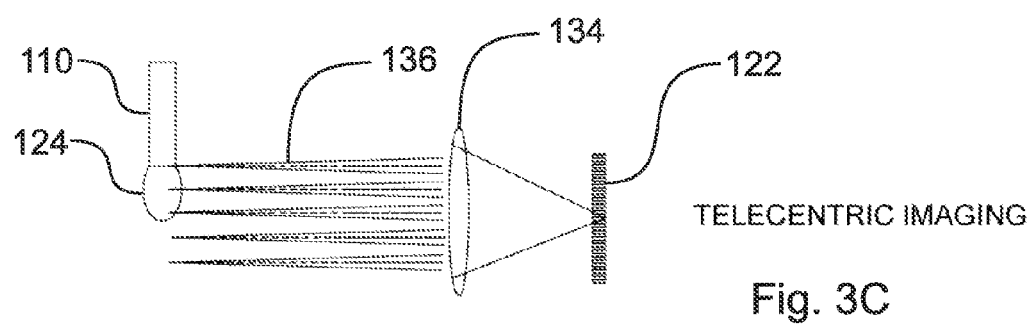
Fig. 3C TELECENTRIC IMAGING
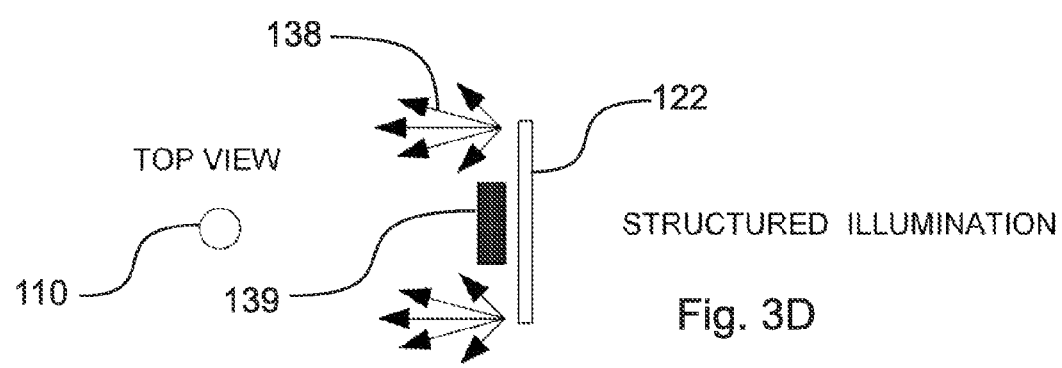
Fig. 3D STRUCTURED ILLUMINATION

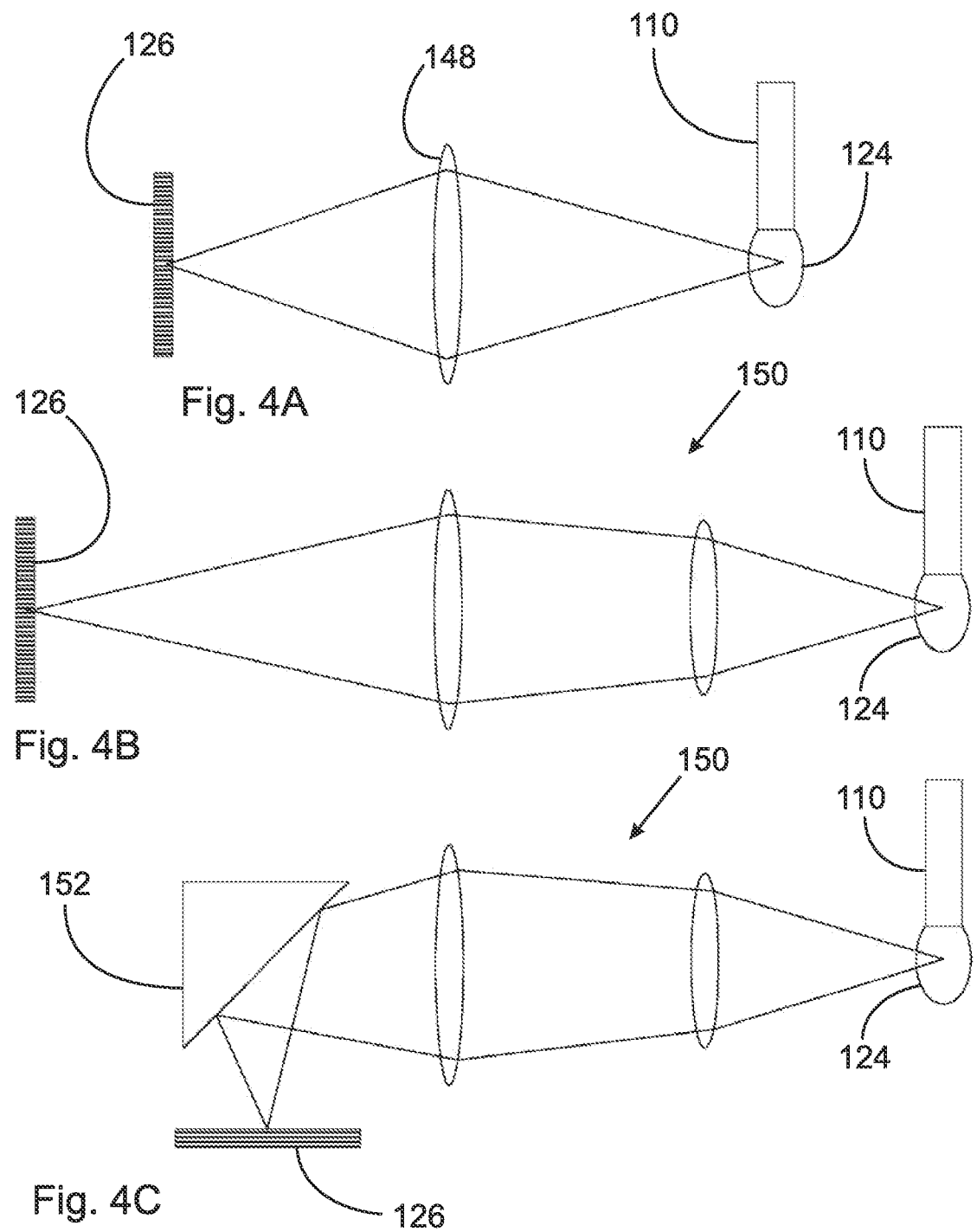

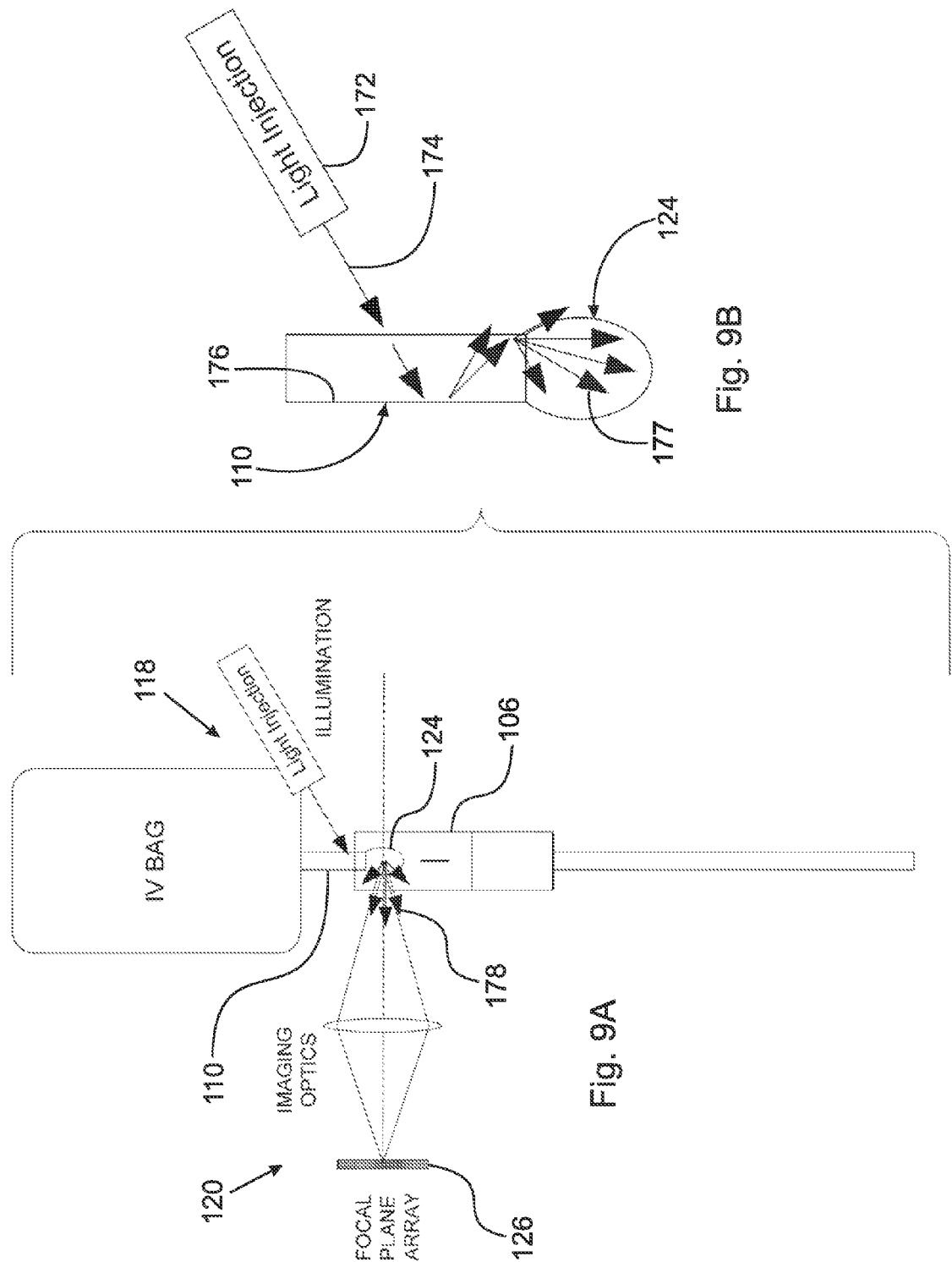

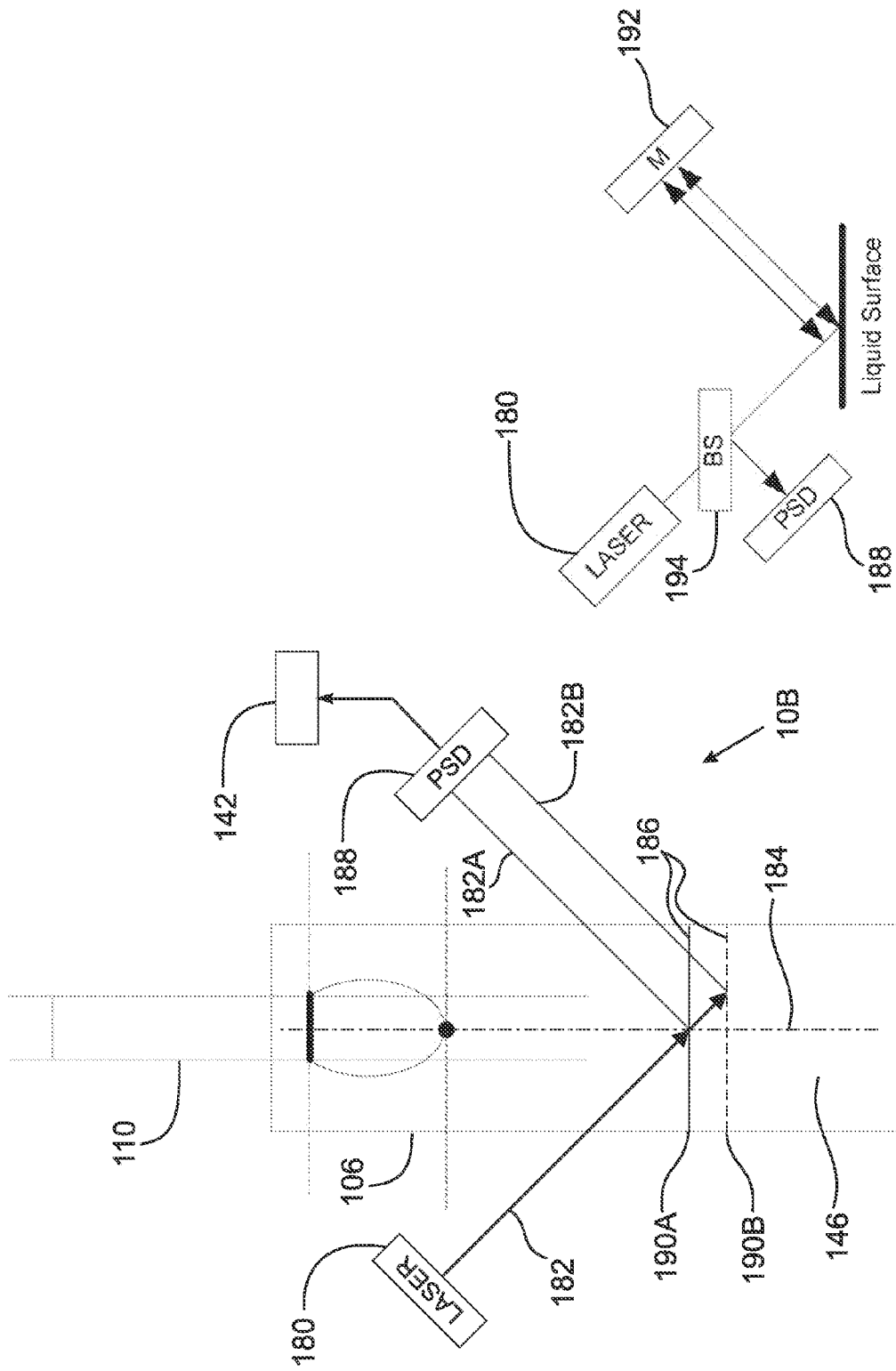

OPTICAL IMAGING SYSTEM FOR AIR BUBBLE AND EMPTY BAG DETECTION IN AN INFUSION TUBE

CROSS REFERENCE TO RELATED APPLICATIONS

This is a continuation-in-part patent application under 35 USC 120 of U.S. patent application Ser. No. 12/907,403 filed Oct. 19, 2010, which application is incorporated herein by reference.

TECHNICAL FIELD

The present disclosure relates generally to an infusion tube with optical imaging for detecting and measuring air bubbles and identifying air-in-line and empty bag conditions.

BACKGROUND

U.S. Pat. No. 4,703,314 broadly teaches an optical in-line air detector. U.S. Pat. No. 5,257,827 teaches an ultra-sonic air sensor for detecting air bubbles over a certain volume for alarm. U.S. Pat. No. 6,049,381 uses optical sensing to differentiate air bubbles from particulate.

The prior art teaches the use of grayscale images for optical sensing in an infusion pump. Unfortunately, boundaries between areas of interest can be difficult to discern in a grayscale image, for example, in the case when intensities are not particularly divergent at the boundaries. This uncertainty results in impaired detection and limits further operations using the images.

SUMMARY

According to aspects illustrated herein, there is provided an optical imaging system for use with an infusion tube having a drip chamber and an output tube. The drip chamber includes a first portion with a drip tube, a second portion with an exit port, and a third portion located between the first and second portions. The optical imaging system includes: an illumination system with at least one light source for emitting light, an optical system, and a memory element configured to store computer executable instructions. The optical system is for receiving the light transmitted by the output tube or the second portion and transmitting data characterizing the received light. The system includes at least one processor configured to execute the computer executable instructions to: detect, using the image, an air bubble in the output tube or the second portion; and determine a volume of the detected air bubble.

According to aspects illustrated herein, there is provided an optical imaging system for use with an infusion tube having a drip chamber including a first portion with a drip tube, a second portion with an exit port, and a third portion located between the first and second portions. The optical imaging system includes: an illumination system including at least one light source for emitting light and an optics system including: first, second, and third lenses for receiving and transmitting the light transmitted through the first, second, and third portions, respectively; and first, second, and third image sensors for: receiving the light from the first, second, and third lenses, respectively; and generating and transmitting data characterizing the light received from the first, second, and third lenses. The imaging system includes a memory element for storing computer executable instructions, and at least one processor configured to execute the computer executable instructions to generate, using the data, first, second, and third images of the first, second, and third portions, respectively.

According to aspects illustrated herein, there is provided a method of imaging an infusion tube having a drip chamber and an output tube, wherein the drip chamber includes a first portion with a drip tube, a second portion with an exit port, and a third portion located between the first and second portions. The method includes: storing computer readable instructions in a memory element; emitting first light from at least one light source; receiving, using an optical system, the first light transmitted by the output tube or the second portion; transmitting, using the optical system, first data characterizing the received first light; and executing, using at least one processor, the computer executable instructions to: detect, using the first image, an air bubble in the output tube or the second portion; and determine a volume of the detected air bubble.

According to aspects illustrated herein, there is provided a method of imaging an infusion tube having a drip chamber including a first portion with a drip tube, a second portion with an exit port, and a third portion located between the first and second portions. The method including: storing computer readable instructions in a memory element; emitting light using at least one light source; receiving and transmitting, using first, second, and third lenses, the light transmitted through the first, second, and third portions, respectively; receiving, using first, second, and third image sensors, the light from the first, second, and third lenses, respectively; generating and transmitting, using the first, second, and third image sensors, data characterizing the light received from the first, second, and third lenses; and executing, using at least one processor, the computer executable instructions to generate, using the data, first, second, and third images of the first, second, and third portions, respectively.

BRIEF DESCRIPTION OF THE DRAWINGS

The nature and mode of operation of the present invention will now be more fully described in the following detailed description of the invention taken with the accompanying drawing figures, in which:

FIGS. 3A through 3F illustrate example embodiments of the illumination system shown in FIG. 2;

FIGS. 4A through 4C are schematic representation of embodiments for an optical system;

FIGS. 9A and 9B are schematic details of a pump using light injection;

FIGS. 10A and 10B are schematic details of a pump with a meniscus detection arrangement;

DETAILED DESCRIPTION

At the outset, it should be appreciated that like drawing numbers on different drawing views identify identical, or functionally similar, structural elements of the invention. While the present invention is described with respect to what is presently considered to be the preferred aspects, it is to be understood that the invention as claimed is not limited to the disclosed aspects.

Furthermore, it is understood that this invention is not limited to the particular methodology, materials and modifications described and as such may, of course, vary. It is also understood that the terminology used herein is for the purpose of describing particular aspects only, and is not intended to limit the scope of the present invention, which is limited only by the appended claims.

Unless defined otherwise, all technical and scientific terms used herein have the same meaning as commonly understood to one of ordinary skill in the art to which this invention belongs. Although any methods, devices or materials similar or equivalent to those described herein can be used in the practice or testing of the invention, the preferred methods, devices, and materials are now described.

Figure 1:
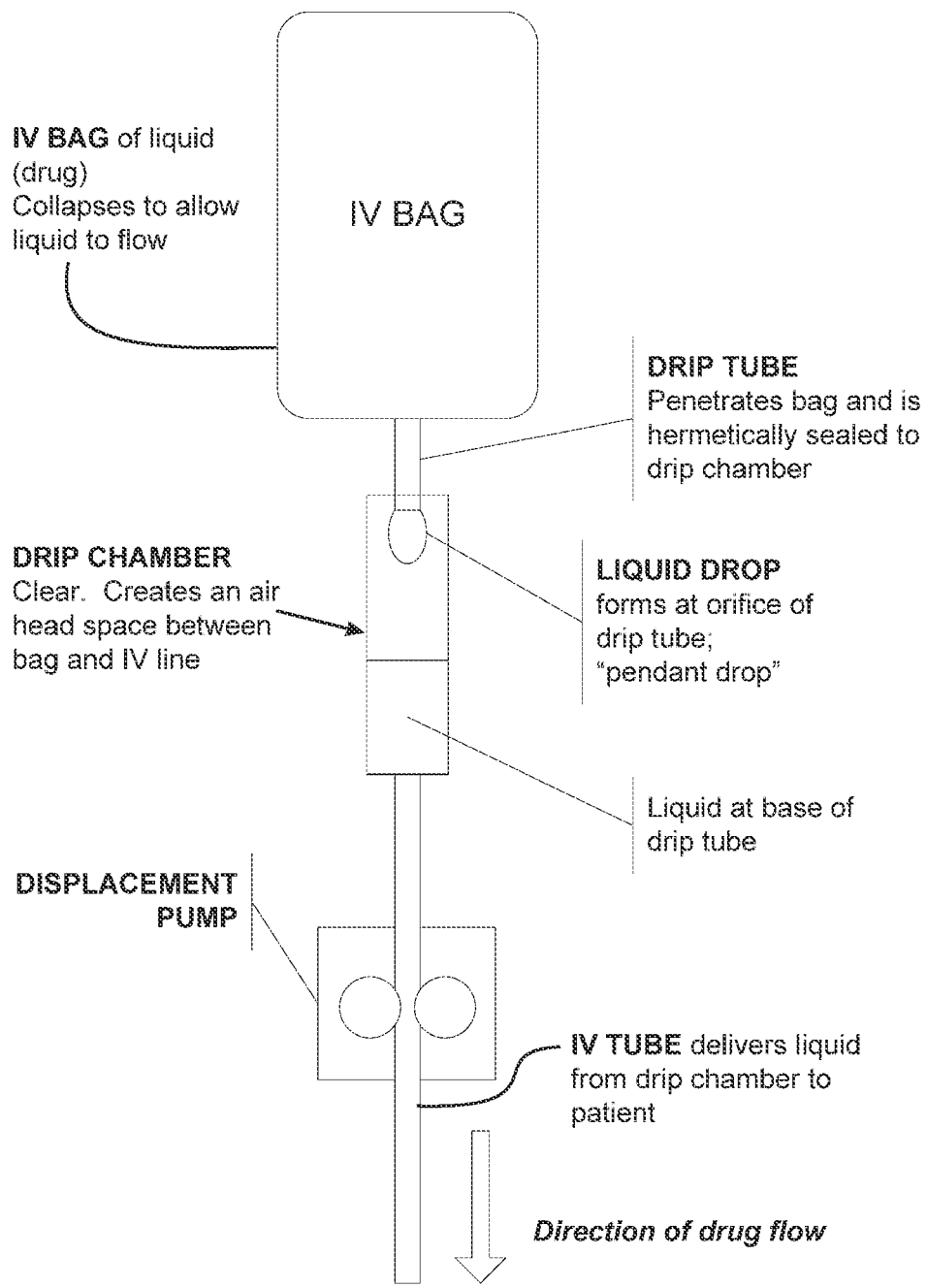
FIG. 1 is a schematic representation of definitions for an infusion pump.

FIG. 1 is a schematic representation of definitions for an infusion pump.

Figure 2:
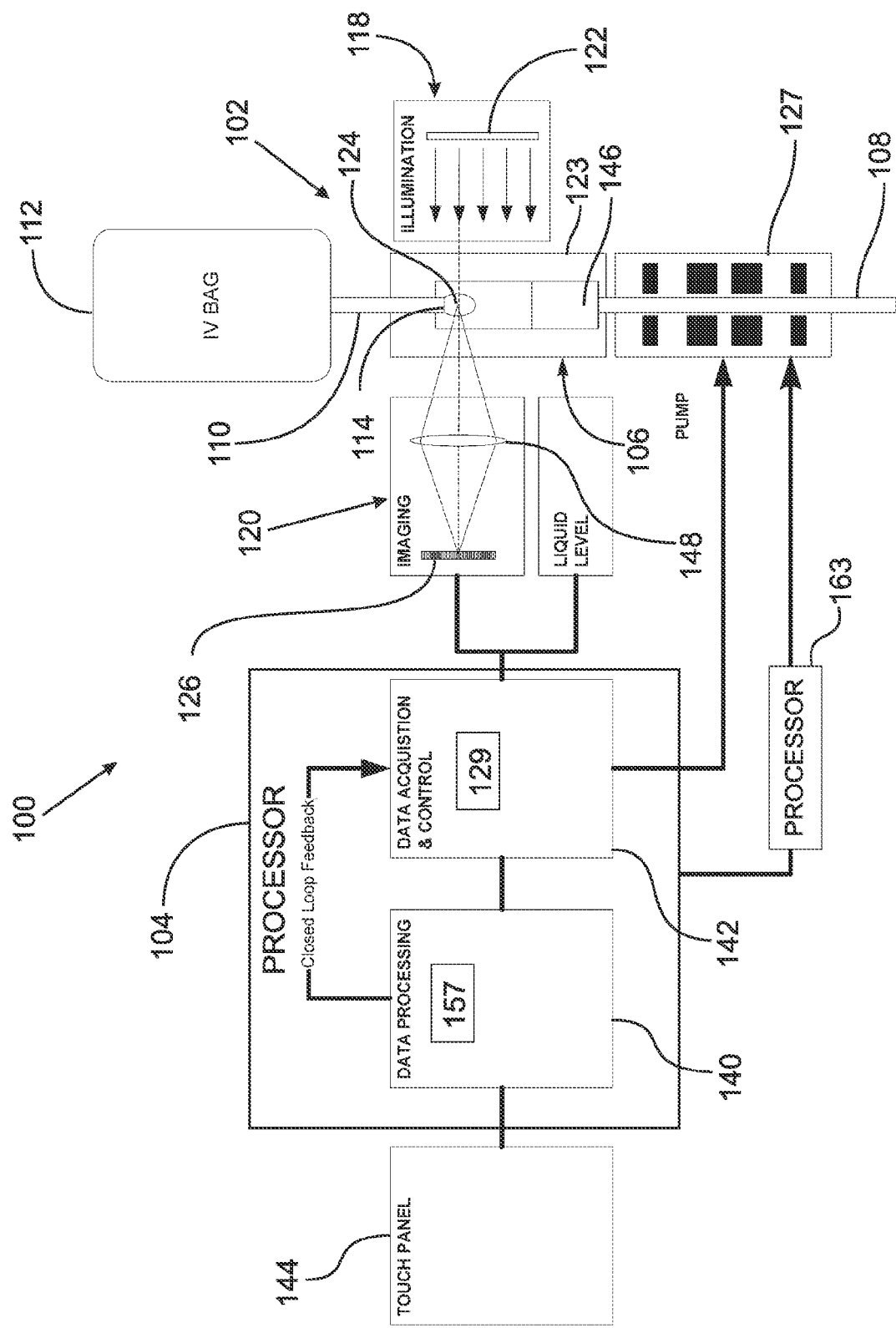
FIG. 2 is a schematic block representation of an infusion pump with an optical imaging system.

FIG. 2 is a schematic block representation of infusion pump 100 with optical imaging system 102. Pump 100 includes specially programmed microprocessor 104, drip chamber 106 for connection to output tube 108, and drip tube 110 for connecting the drip chamber to a source of fluid 112, for example, an IV bag. The drip tube includes end 114 disposed within the drip chamber. The imaging system includes illumination system 118 and optical system 120. System 118 includes lighting element 122 for transmitting light through wall 123 of the drip chamber to or around drop 124 of the fluid suspended from the end of the drip tube, for example, one or both of the drip and end 114 are illuminated. System 118 also controls illumination properties of the light transmitted to the drop. System 120 receives, for example using optical sensor 126, light transmitted through the drop, or through or around end 114 and transmits, to the microprocessor, data 129 regarding the received light. Pump 100 also includes pumping mechanism 127. In one embodiment, the mechanism includes top and bottom flow restrictors and uses peristaltic actuators, such as rollers, to displace fluid through tube 108.

Figure 3E:
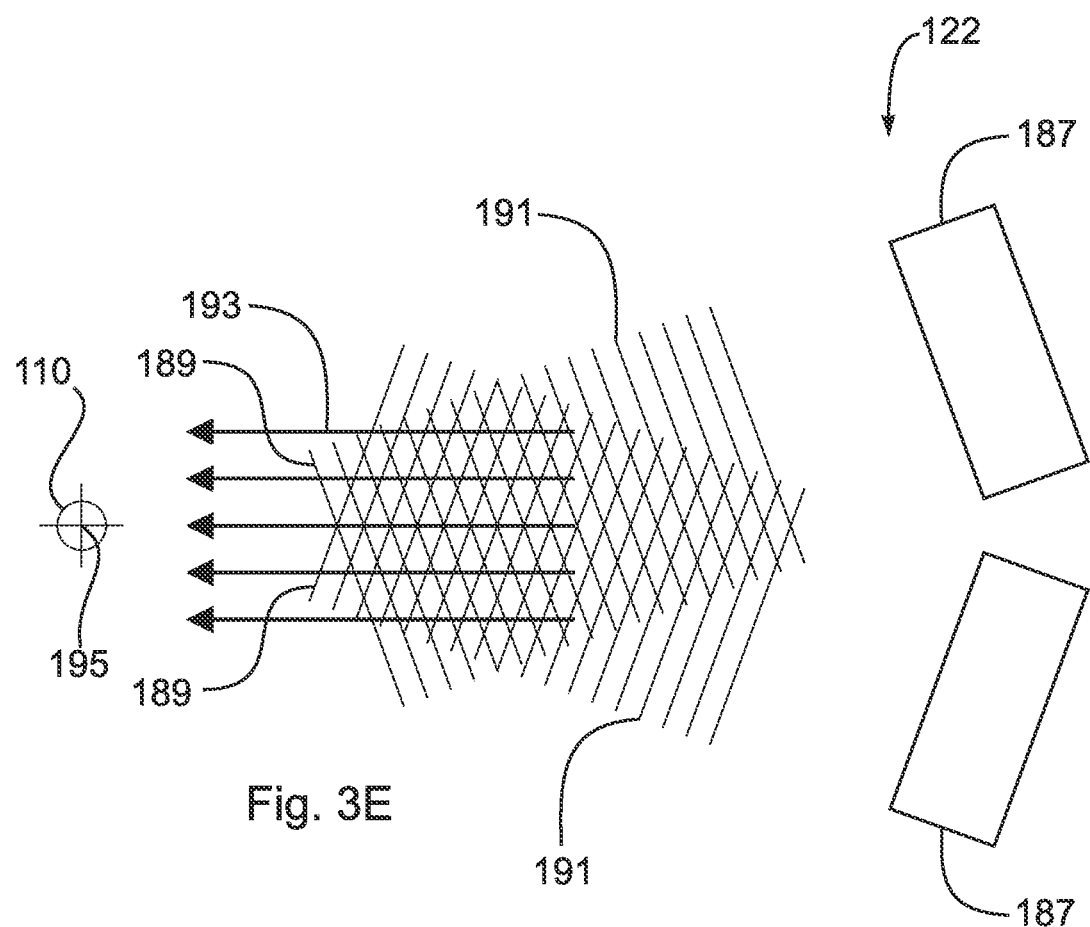

FIGS. 3A through 3F illustrate example embodiments of system 118 in FIG. 2. As shown in FIG. 3A, light rays 128 from a collimated illumination system are parallel. As shown in FIG. 3B, light rays 130 from a diffuse illumination system are emitted in a cone-shaped pattern from each light emitting point on an illumination plane. As shown in FIG. 3C, light rays 132 from illumination source 122 pass through telecentric lens 134 and are formed into ray bundles 136. The rays in bundles 136 are very nearly parallel. The ray bundles provide sharp definition of image edges and minimize depth distortion As shown in FIG. 3D, a structured lighting element shapes illumination, for example, rays 138, so as to control unwanted or stray light and to accentuate edges of an objecting being illuminated. A structured lighting element can include barrier 139, disposed between an illumination source and an object being illuminated, for example, drop 124, to shape the illumination, for example, by blocking or altering light emanating from the source.

FIG. 3E illustrates the use of laser interference to project stripe patterns measure drop 124. Illumination source 122 includes laser light sources 187. Sources 187 project light patterns consisting of many stripes at once, or of arbitrary fringes. This technique enables the acquisition of a multitude of samples regarding an image of drop 124, simultaneously. As seen from different viewpoints, the projected pattern appears geometrically distorted due to the surface shape of the object. In one embodiment, patterns of parallel stripes are used; however, it should be understood that other patterns can be used. The displacement of the stripes allows for an exact retrieval of the three dimensional (3D) coordinates of details on an object's surface, for example, the surface of drop 124. Laser interference works with two wide planar fronts 189 from laser beams 191. The interference of the fronts results in regular, equidistant line, or interference, patterns 193. Different pattern sizes can be obtained by changing the angle between the beams. The method allows for the exact and easy generation of very fine patterns with unlimited depth of field. FIG. 3E is a top view of pump 100 and sources 187 are shown disposed radially about axis 195 for drop tube 110. However, it should be understood that other configurations of sources 187 with respect to the pump are possible, for example, parallel to axis 195.

Figure 3F:
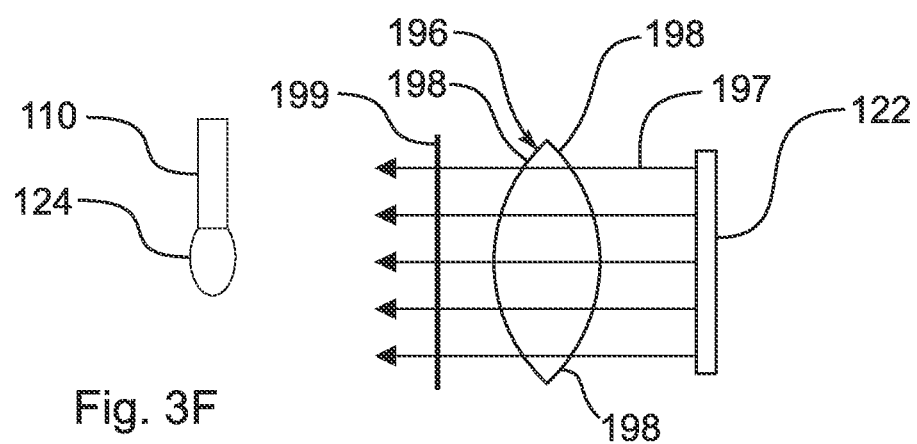

FIG. 3F illustrates the use of projection lens 196 in system 118. In FIG. 3F, system 118 illumination source transmits light 197 through lens 196. Surface 198 of the lens is modified as known in the art, for example, etched or through deposition of chrome or other materials, to produce a pattern on the surface. Light 197 passing through the lens projects an image of the pattern on and about drop 124. In one embodiment, projected pattern 199 is in the form of a constant-interval bar and space square wave, such as a Ronchi Ruling, or Ronchi grating.

The illumination source for a structured lighting element can be collimated, diffuse, or telecentric. Structured illumination can control unwanted or stray light and accentuate image edges. In one embodiment, the illumination system includes a telecentric lighting element. In one embodiment, the illumination system includes a structured lighting element.

Returning to FIG. 2, microprocessor 104 includes data processing segment 140 and data acquisition and control segment 142. The pump also includes control panel 144, for example, any graphical user interface known in the art. Output from the optical system, for example, data 129 from sensor 126, is inputted to segment 142. Panel 144, or other operator input, is used to input a desired flow rate through the drip chamber, as well as other necessary data such as drug type and treatment information. Microprocessor 104 can be any microprocessor known in the art.

Pump 100 uses optical sensing of pendant drops, that is drops hanging from or suspended from end 114, to measure fluid flow through the drip chamber to the output tube and to provide input to a closed-loop pump control process controlled by the microprocessor. Fluid from source 112 flows through drip tube to end 114 of the drip tube. The fluid forms drop 124 at end 114 and when conditions in the drip tube, discussed infra, are suitable, the drop falls from end 114 into fluid 146 in the drip chamber. In general, a pendant drop increases in size in proportion to the outflow of fluid 146 from the drip chamber through tube 108. That is, an increase in the volume of the pendant drop during a time frame is equal to the volume of fluid passing from the drip chamber to tube 108 in the time period. The preceding relationship is based on the following assumptions: the fluid from the source is not compressible; source 112, the drip tube, the drip chamber, tube 108, and a patient to whom tube 108 is connected are closed to outside atmosphere. Each measurement of the drop volume is processed to provide a fluid volume (or mass) measurement. Successive measurements of drop volume over known intervals of time are used by the microprocessor to calculate the flow rate of fluid through the system.

Thus, in one embodiment, operation of pumping mechanism 127 is controlled by the microprocessor using the desired set point for flow through the drip chamber and data regarding a measured flow rate of fluid through the drip chamber. For example, the microprocessor executes a feedback loop which compares the desired flow rate with the measured flow rate, and adjusts the pumping mechanism to correct any deviations between desired and measured flow rates.

FIGS. 4A through 4C are schematic representation of embodiments for optical system 120. The embodiments shown in FIGS. 4A through 4C form real, conjugate images, for example, of drop 124 on a focal plane array formed by sensor 126. FIGS. 4A and 4B use refractive optics, such as single lens 148 or combinations 150 of lenses, respectively. FIG. 4C shows refractive optics, such as combination 150 of lenses, and reflective optics, such as fold mirror 152. Lens 148, combination 150, and mirror 152 can be any lens, combination of lenses, or mirror known in the art. Combination 150 may include different lenses in FIGS. 4B and 4C.

Returning to FIG. 2, in one embodiment, optical sensor 126 is a focal plane array formed by any means known in the art, including, but not limited to a charge coupled device (CCD), a CMOS detector, or a hybrid imaging array such as InGaAs bonded to a CMOS readout integrated circuit. System 120 includes optics, such as lens 148, focused on the location of drop 124. It should be understood that other optics can be used in system 120. In one embodiment, chamber 106 is substantially optically clear and system 118 directs light though the walls of the chamber to the optical system, for example, sensor 126. The light can provide back or side illumination of the drop. In one embodiment, system 102 is configured such that drop 124 and the focal plane array are optical conjugates and the focal plane array records an actual image of the drop. The imaging system captures drop images at a rate sufficient to observe the growth and detachment of a single drop.

In one embodiment, pump 100 satisfies two key metrics with respect to imaging drop 124. First, the frame rate (images per second) is sufficient to capture a sequence of images as the drop grows in size and detaches. Second, the exposure time (the amount of time the light is collected on the sensor for each specific image) is short enough to freeze the motion of the drop. Pump 100 generates images with clear edge definition, sufficient magnification (in terms of number of pixels across the drop), and a minimum number of artifacts such as glare.

In one embodiment, imaging system 102 and the microprocessor produce an accurate image of the drop that is then analyzed as described infra to determine the volume of the drop. Since the fluid drop has a uniform density, and any bubbles (occlusions) or entrainments are sufficiently small to be negligible, in one embodiment, only the outer surface of the drop is measured to calculate the volume of the drop. The preceding measurement is accomplished by imaging the drop with sufficient spatial resolution to accurately measure the boundary surface. A numeric integral over this boundary then provides the droplet volume.

Figure 5C:
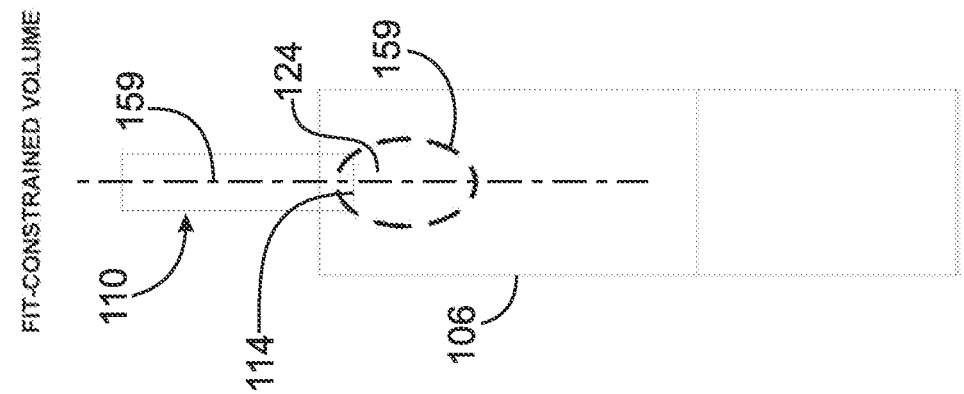
FIGS. 5A through 5C illustrate imaging processing definitions.
Figure 5B:
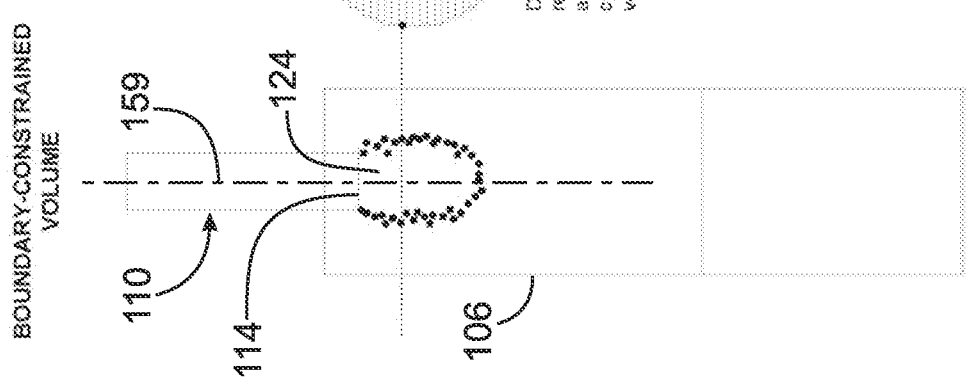
Figure 5A:
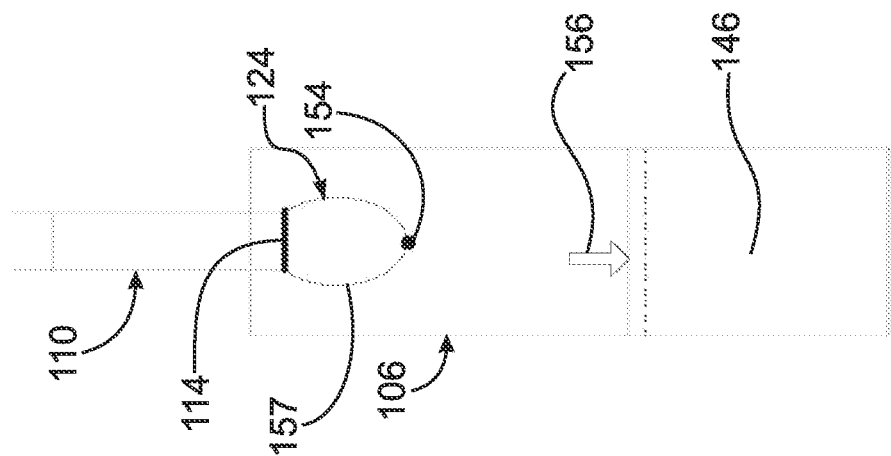

FIGS. 5A through 5C illustrate imaging processing definitions. In one embodiment, a reference/alignment frame and an image scale (pixels per mm) are established by locating end point 114 of the drip tube orifice, as shown in FIG. 5A. The end point has a known size and hence provides scale calibration. The end point also represents the top boundary of the drop, which is used in volume calculations described infra. In one embodiment, apex 154 of the drop (a point furthest from the fixed/reference point) is identified and used in the determination of the volume of the drop. For example, the optical system, for example, sensor 126, receives the light transmitted into or through the drip tube and transmitting, to the microprocessor, data regarding the received light. In one embodiment, the microprocessor is for determining, using the data, a boundary of end point 114 and using the boundary of end point 114 as a reference point for determining a volume, shape, or location of the drop, as further described infra.

In one embodiment, as further described infra, the direction of gravity (gravity vector 156) with respect to drop 124 is determined. A reference point, for example, the boundary of end point 114, and the gravity vector are used to establish a reference frame for the image processing.

In one embodiment, volume of drop 124 is calculated by using the microprocessor to receive data 129 and generate an image of the drop from the data. The microprocessor locates an outer edge of the drop in the image to define boundary 157 of the drop. The microprocessor integrates an area enclosed by the boundary and calculates a volume of revolution for the drop with respect to axis 159 for the drop that intersects the end of the drip tube, assuming symmetry of the drop with respect to the axis.

The above calculation of the volume of drip 124 can be calculated using at least two broad approaches. The first approach, termed Boundary Constrained Volume and shown in FIG. 5B, uses the outer location of the drop image to calculate the total volume. Each horizontal row 158 of pixel data from the image has associated with it an outer left and right boundary. The area between these boundaries is treated as the two dimensional projection of a circular disk volume (the symmetric volume of rotation of the area). The drop image is integrated from end point 114 to the apex by summing the volume of each row. Boundary Constrained Volume obtains maximum resolution for each row of data.

The second approach is termed Fit Constrained Volume and is shown in FIG. 5C. That is, the volume of drop 124 is determined by fitting a parametric function to the boundary image of the drop and integrating the parametric function, again, assuming rotational symmetry. There are a number of possible fitting algorithms, as discussed below, but the result of any fit is a set of parameters to the assumed function that represents entire boundary 157. Fit Constrained Volume smoothes out row detail.

In one embodiment, the microprocessor creates a plurality of temporally successive images of the drop from data 129 and calculates a respective volume for the drop in each successive image or calculates respective time periods between detachment of successive drops from the end of the drip tube. By temporally successive images, we mean a series of images taken over a time period in chronological order. The microprocessor calculates a rate of increase for the volume of the drop using the respective volumes or the respective time periods. As noted above, flow out of the drip tube is substantially equal to the increase in the volume of the drop; therefore, the time periods between drops detaching from the end of the drip tube can be correlated to the volume increases of the successive drops. For example, in one embodiment, the microprocessor calculates a respective volume for the drop in each successive image, for example, using operations described infra and supra; calculates changes in the respective volumes; and calculates a flow rate of fluid to the output tube based on the changes in the respective volumes. In one embodiment, the microprocessor controls mechanism 127 to match the calculated flow rate with a desired flow rate, for example, stored in the microprocessor.

In one embodiment, the microprocessor is for generating a free flow alarm or an out of bound condition alarm when the rate of increase for the volume of the drops exceeds a predetermined value, for example, stored in the microprocessor. In one embodiment, the microprocessor is for operating mechanism 127 to shut off flow to the output tube when the free flow alarm or the out of bound condition alarm is generated. In one embodiment the microprocessor generates a downstream occlusion alarm when the rate of increase of the volume of the drop is less than a predetermined value. In one embodiment, the microprocessor determines that a drop is absent from the end of the drip tube for a specified period of time and generates an empty bag alarm or an air-in-line alarm.

In one embodiment, the pump includes processor 163 used to operate mechanism 127 to shut off flow to the output tube when the free flow alarm or the out of bound condition alarm is generated. That is, as a safety and redundancy factor, a second microprocessor is used in the pump.

The drop is initially hanging from a fixed point in the drip chamber, for example, end 114. In one embodiment, the microprocessor is for identifying when the drop detaches from the fixed point in the drip chamber as a means of determining when the drop has reached maximum volume. The microprocessor makes the preceding identification by creating a plurality of temporally successive images of the drop and analyzing these images. By temporally successive images, we mean a series of images taken over a time period in chronological order.

In one embodiment, the microprocessor identifies, in each successive image, a respective point in the boundary, for example, apex 154, and determines a distance of each respective point from end 114. The microprocessor then identifies two successive images of the drop in which the distance, noted above, in the second image in the succession is less than the distance in the first image in the succession. This decrease of the distance indicates that the drop detached from the fixed point in the interval between the first and second images, which further indicates that the drop reached a maximum size in the first image. The microprocessor calculates the volume of the drop using the first image.

Figure 6:
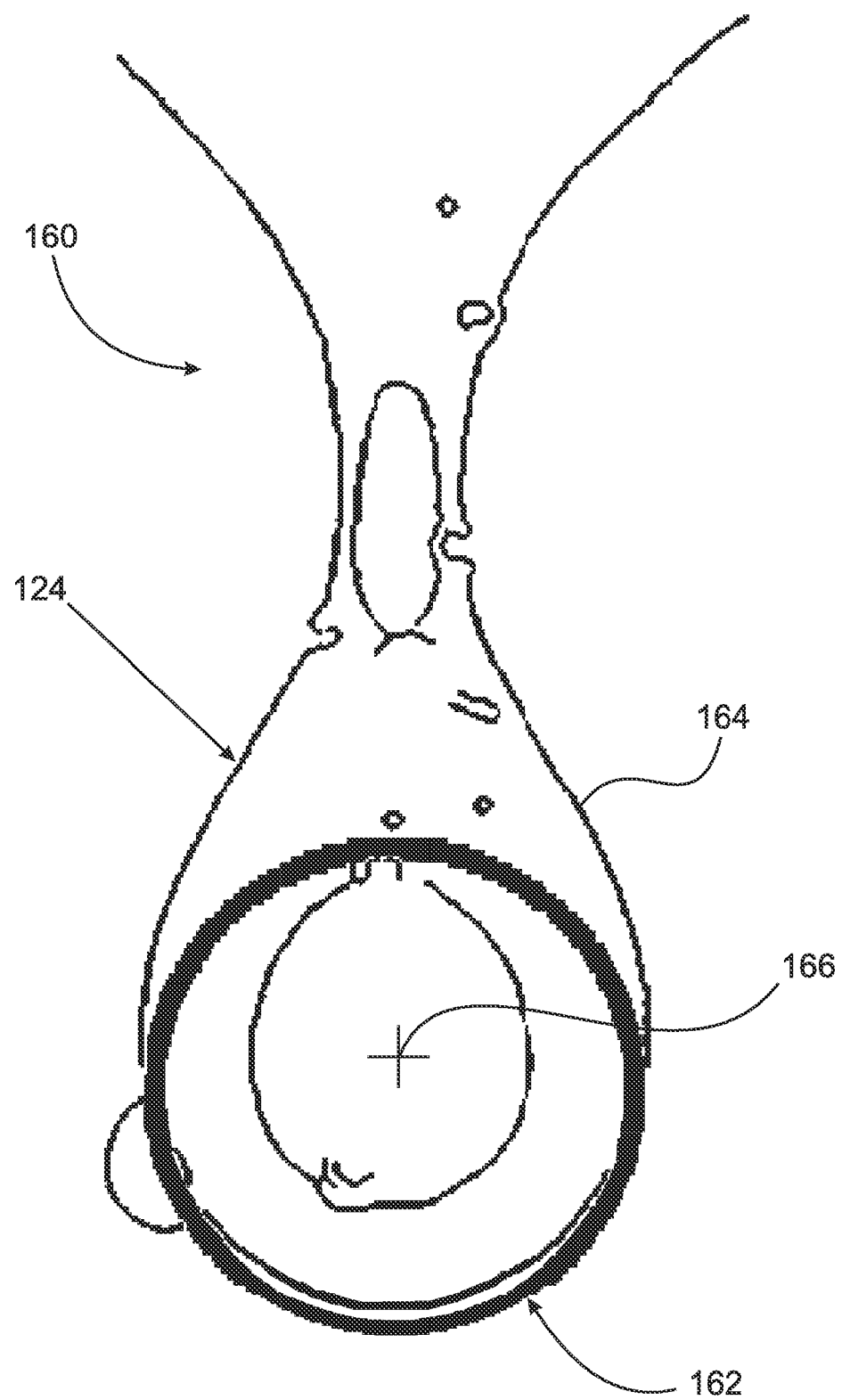
FIG. 6 illustrates an image of a drop including a circle at least partly included within an outer boundary of the drop

FIG. 6 illustrates image 160 of drop 124 including circle 162 at least partly included within outer boundary 164 of the drop. FIG. 6 illustrates a specific example of the Fit Constrained Volume approach. In one embodiment, the microprocessor identifies respective circles 162 within each temporally successive image. The circles are partially defined by a respective outer boundaries 164 of the temporally successive images. The microprocessor identifies a respective location, with respect to the fixed point in the drip chamber, for each respective circle and calculates a volume of the drop from the data and using the respective circles.

In one embodiment, identifying the respective location for said each respective circle includes identifying the image corresponding to the largest size of the drop, for example, the last image before the drop detaches from the end point of the drip tube. For example, the microprocessor identifies a respective point on each respective circle at a furthest distance from the fixed point in the drip chamber, for example, end point 114. The microprocessor then determines which of the respective points is furthest from the fixed point and identifies an image including the respective point furthest from the fixed point. That is, the microprocessor identifies the largest drop by identifying the drop having the largest circle. In one embodiment, the largest drop is identified by determining a first image in which the distance of the apex from the fixed point decreases with respect to the distance of the apex from the fixed point for a second image immediately preceding the first image. This decrease indicates that the drop detached from the fixed point in the interval between the first and second images, which further indicates that the drop reached a maximum size in the first image. The microprocessor calculates the volume of the drop using the image including the respective point furthest from the fixed point.

In one embodiment, the microprocessor identifies the respective outer boundaries for each of the temporal images such that each outer boundary includes a respective edge of the drop furthest from the fixed point in the drip chamber and the respective circle includes the respective edge. That is, the microprocessor aligns the circles described supra with the actual edges of the drops such that the points of the circles furthest from the fixed point, for example, end 114, are part of the edge of the drop. In one embodiment, the microprocessor identifies respective circular arcs corresponding to the respective edges and including the respective circular arcs in the respective circles.

In one embodiment, identifying the image corresponding to the largest size of the drop, for example, the last image before the drop detaches from the end point of the drip tube, includes using the center points of the circles. For example, the microprocessor calculates respective center points 166 for the circles and calculates the positions of the center points with respect to the fixed point, for example, end point 114. The microprocessor then determines which of the center points is furthest from the fixed point and identifies an image including the center point furthest from the fixed point. That is, the microprocessor identifies the largest drop by identifying the drop having the largest circle. The microprocessor calculates the volume of the drop using the image including the center point furthest from the fixed point.

Figure 7:
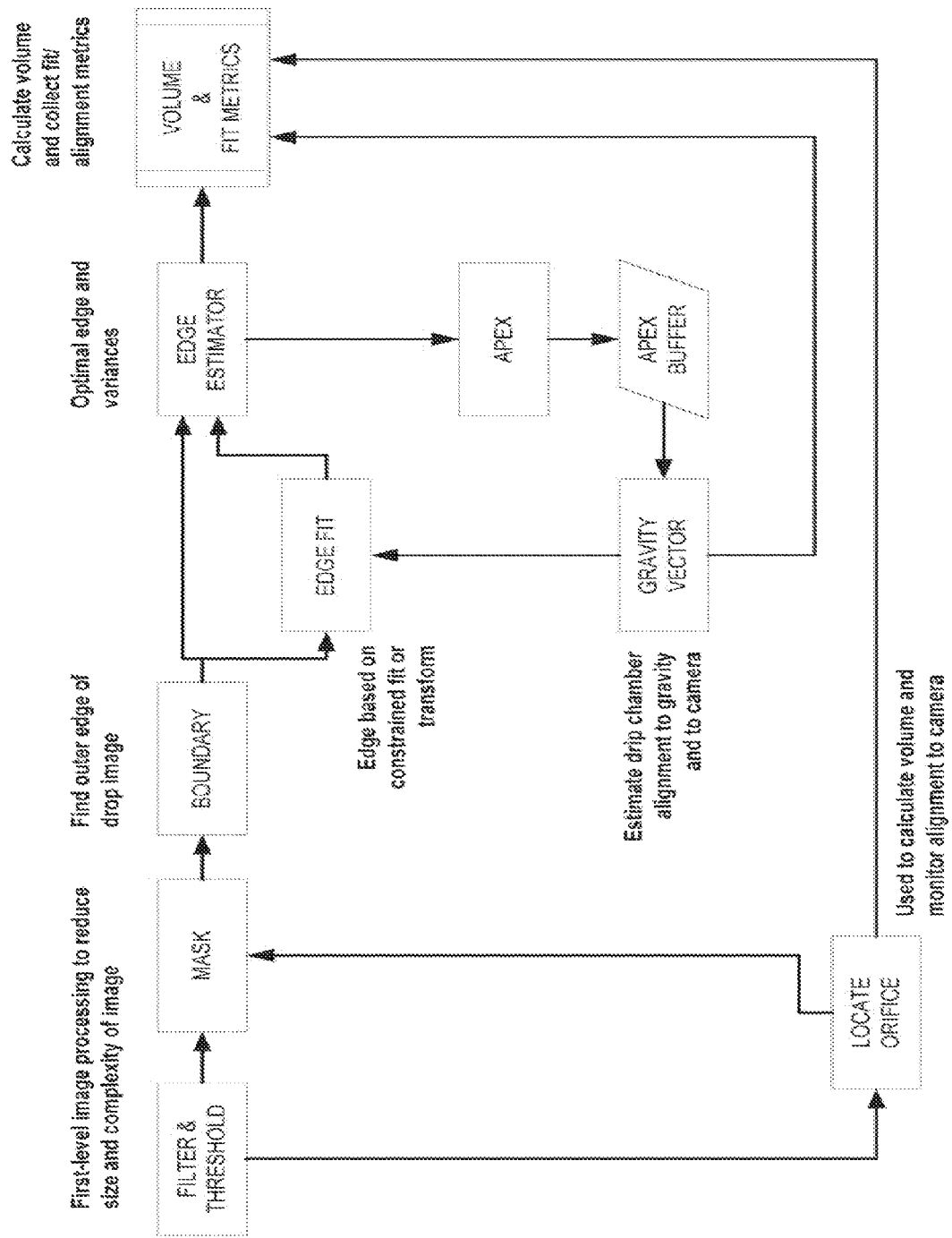
FIG. 7 is a flow chart illustrating operation of a pump with an optical imaging system.

FIG. 7 is a flow chart illustrating operation of pump 100 with an optical imaging system. FIG. 7 illustrates an example algorithm usable by pump 100. It should be understood that other algorithms are usable by the pump. The image of drop 124 is filtered and thresholded to create a binary image. Filter operations can include median filtering (to remove isolated glare), background and image uniformity correction (to remove noise sources due to dark noise, read noise, pixel non-uniformity, and illumination non-uniformity), and edge definition (using techniques such as convolution or unsharp masking). The resulting images are thresholded to yield binary images. A binary image consists of values that are either black or white, with no intermediate grayscale values.

The images are also processed (in parallel with the above operations) to find the reference location, for example, end point 114, using techniques such as feature detection, pattern matching, or transform techniques such as the Radon transform. The end point location is used to form an image mask. A mask isolates a region of an image for further processing. Use of a mask increases computational speed, as well as eliminates artifact information from being further processed.

In one embodiment, the binarized, masked images are then processed row-by-row to find the extreme right- and left-boundaries. This boundary-constrained fit is one estimate of the drop edge shape. In one embodiment, the images are also processed using a fit-constrained algorithm. Such an algorithm applies constraints based on assumptions about the drop shape as discussed supra and infra. The constraints are used in a non-linear least squares optimization scheme to minimize the error between the parameterized constraint function(s) and the set of binarized edge images.

The two different edge approximations are provided to an Edge Estimator algorithm that compares fit-constrained images to boundary-constrained images. In the simplest instantiation, the images are compared row-by-row. The boundary-constrained images are considered to be the "correct" result unless they deviates from the fit-constrained images by more than a certain parameter (this parameter is adjusted during calibration). If the deviation is too large, the value from the fit-constrained image is used to replace that of the boundary-constrained image for that row. The above is intended to illustrate the concept behind the estimator. In actual use, more sophisticated algorithms are used to simultaneously optimize the difference between the two initial estimates. An example of such an algorithm is a Kalman filter, but other algorithms familiar to those skilled in the art may also be utilized.

The output from the Edge Estimator also provides the location of the apex of the drop, which is for example, used to calculate the time-dependent gravity vector. This operation requires access to prior estimates of the apex value (to calculate the change), and hence a number of prior values are stored in a buffer. The gravity vector is required for some of the parametric fit functions that are used in the fit-constrained edge estimation algorithms. Hence, the gravity vector is used in a feedback loop for the edge fit algorithms.

Figure 8A:
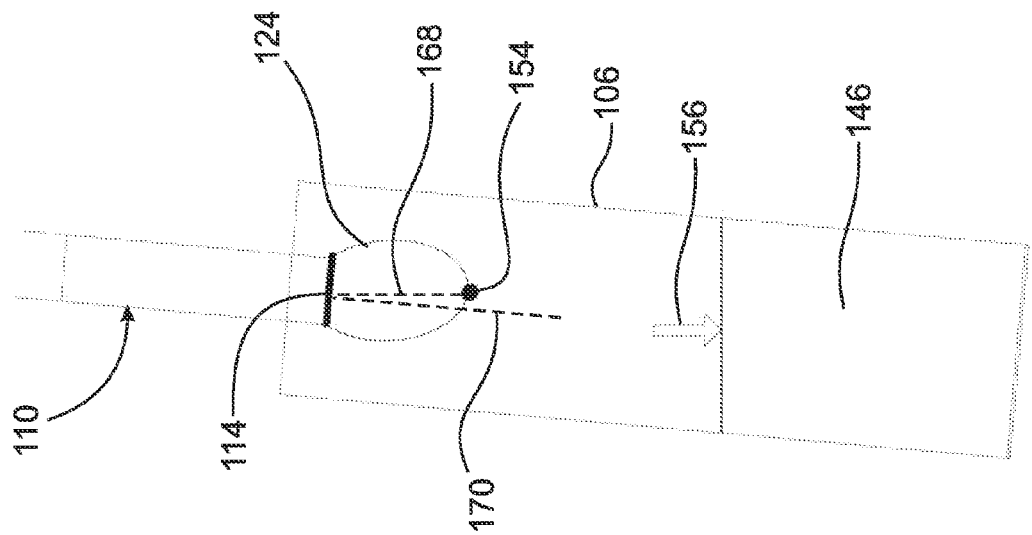
FIGS. 8A and 8B are schematic details for a pump implementing an operation for determining a gravity vector.
Figure 8B:
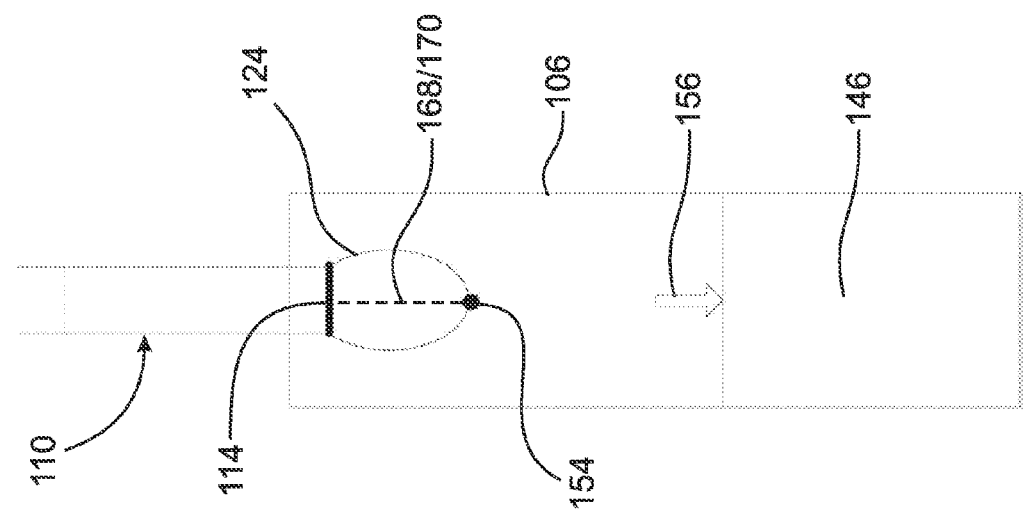

FIGS. 8A and 8B are schematic details for pump 100 implementing an operation for determining gravity vector 156. In one embodiment, system 118 illuminates end point 114 and drop 124 and the optical system, for example, sensor 126, receives light emanating from the end point and light emanating from the drop and transmits data 129 regarding the received light. The microprocessor generates, using the data, respective images of the drop and the end of the drip tube and locates an apex of the drop, the apex being a portion of the drop at a furthest distance from the end of the drip tube. The microprocessor determines, using the location of the apex, an orientation of the drop with respect to the end of the drip tube and calculates, using the orientation of the drop with respect to the end of the drip tube, an orientation of the drip chamber. In one embodiment, the microprocessor compares the orientation of the drip chamber to a set point, for example, a certain orientation with respect to plumb stored in the microprocessor, and generates an out of bound condition alarm when the orientation equals the set point or varies from the set point by a specified amount. For example, if the drip chamber is too far out of plumb, operation of pump 100 may be compromised and the alarm is generated.

For example, in FIG. 8A line 168 for the actual orientation of the drop and axis 170 for the drip chamber are co-linear, Since the drop must necessarily align with the forces of gravity (is plumb), the drip chamber is in a plumb orientation in FIG. 8A. Also, line 168 is aligned with gravity vector 156. In FIG. 8B, lines 168 and 170 are not co-linear and the drip chamber is not plumb. Thus, in one embodiment, the microprocessor generates lines 168 and 170 and compares the respective locations or orientation of the lines. That is, the microprocessor calculates the orientation of the drip chamber with respect to the gravity vector. In one embodiment, when data 129 is used to generate respective images over a period of time (temporally sequential images), the gravity vector is determined by measuring in the images of the end of the drip tube and the drop, the location of the apex of the pendant drop as it grows over time and tracking the time-dependent directional change of the apexes over a series of these measurements. In one embodiment, the boundary of end 114 is calculated as described supra and the boundary is used as reference plane for calculating the orientation of the drop and/or the drip chamber.

In one embodiment, the illumination system controls illumination properties of the light illuminating the end of the drip tube and the drop and the microprocessor: identifies respective boundaries of the end of the drip tube and the drop from the respective images; fits a parametric function to the respective boundaries; and integrating the parametric function to obtain a volume of the drop, for example, as described above.

In one embodiment, the end point location, gravity vector, and optimal edge estimate are input to a volume calculation routine that integrates the edge image using the "circular disk" assumption discussed above. The location of the end of the drip tube is used to determine the upper limit of integration, while the gravity vector is used to determine the direction of the horizontal (at right angles to the gravity vector). These end and gravity data values are provided along with the volume as output from the algorithm. In one embodiment, the algorithm also passes out the parameters of the edge fit, as well as statistical data such as fit variances. In one embodiment, the preceding information is used in the digital signal processing chain discussed below.

A number of methods can be used to fit a constraint to the measured image. In one embodiment, a "pendant drop" approach, involves solving the Laplace-Young equation (LYE) for surface tension. A drop hanging from a contact point (the end point) has a shape that is controlled by the balance of surface tension (related to viscosity) and gravity. The assumption is only strictly valid when the drop is in equilibrium; oscillations (due to vibration or pressure fluctuations) will distort the drop shape from the Laplace-Young prediction. However, small oscillations will not cause the fit to fail; in fact, the deviation from a fit is itself a good indicator of the presence of such oscillations.

In one embodiment, a Circular Hough Transform (CHT) is used on the image to identify the component of the image that represents the curved bottom of the drop. While not strictly a "fit", the CHT provides a parametric representation of the drop that is characterized by the value and origin of the radius of a circle. The CHT algorithm is representative of a constraint that is determined or applied in a mathematical transform space of the image. Other widely-used transforms, familiar to those skilled in the art, are the Fourier and wavelet transforms, as well as the Radon transform.

The parametric fitting procedures described above apply strong constraints on the possible location of the edge of the drop. Along with the assumption of continuity (a fluid edge cannot deviate from its neighbors over sufficiently short distances), and the requirement that the drop edge terminate at the drip tube orifice, the procedures are used to augment and correct the boundary-constrained image, as discussed above. Other fitting procedures work similarly to those discussed herein.

FIGS. 9A and 9B are schematic details of pump 100 using light injection. Drip tube 110, drip chamber 106, tube 108, drop 124, imaging system 120, and sensor 126 are as described for FIG. 2. Illumination system 118 includes illumination source 172 for transmitting, or injecting, light 174 into the drip tube. The light reflects off a plurality of portions of internally facing surface 176 of the drip tube and the reflected light is transmitted through the end point 114 of the drip tube into interior 177 of drop 124 such that the interior is uniformly illuminated. The optical system receives light 178 transmitted from the interior of the drop and transmits, to the computer processor, data regarding the received light. The data regarding the received light can be operated upon using any of the operations noted supra. For example, in one embodiment, the illumination system is for controlling illumination properties of the light transmitted to the drop, and the optical system is for receiving light from the drop. The microprocessor is for: generating an image from the data, the image including a boundary of the drop; fitting a parametric function to the boundary of the drop; and integrating the parametric function to obtain a volume of the drop.

Thus, light 174 is formed into a beam, which is injected into the transparent drip tube so as to undergo significant internal reflection (i.e., equal to or greater than the so-called "critical angle"). The cylindrical bore of the tube causes the internal reflections to diverge inside the tube (filling the bore of the tube), while imperfections in the tube surface introduce light scattering. The result is that the drop is illuminated internally. Under these conditions the imaging optics in system 120 receive only light that is scattered from the drop surface (there is no direct ray path for the light to reach the lens). In addition to a high contrast edge image, this approach enables the use of a very compact illumination element.

FIG. 10A is a schematic detail of pump 100 with a meniscus detection arrangement. Drip tube 110, drip chamber 106, tube 108, and fluid 146 are as described for FIG. 2. Imaging system 102 includes light source, for example, a laser, for transmitting light 182 at an acute angle with respect to longitudinal axis 184 for the drip chamber, into the drip chamber such that the light reflects, at the acute angle, off a surface 186 of fluid pooled within the drip chamber. System 102 also includes sensor, or position sensitive detector, 188 for receiving reflected light 182 and transmitting, to the computer processor, data regarding the received light. The microprocessor is for calculating a position of surface 186 using the data regarding the received light.

The location on sensor 188 receiving light 182 depends on the location of surface 186. Levels 190A and 190B show two possible levels for fluid 146 and hence, two possible locations for surface 186. As seen in FIG. 10B, light 182A and 182B reflecting from levels 190A and 190B, respectively, strike different portions of sensor 188. The microprocessor uses the difference between the locations on sensor 188 to determine the level of fluid 146, that is, the meniscus, in the drip chamber. Sensor 188 can be any positional sensitive detector known in the art, for example, a segmented sensor or a lateral sensor. In one embodiment, the microprocessor generates an empty bag alarm or an air-in-line alarm for an instance in which the light transmitted from light source 188 is not received by the optical system, for example, the drip chamber is empty or level 186 is so low that light 182 does not strike fluid 146.

A segmented positional sensitive detector includes multiple active areas, for example, four active areas, or quadrants, separated by a small gap or dead region. When a symmetrical light spot is equally incident on all the quadrant, the device generates four equal currents and the spot is said to be located on the device's electrical center. As the spot translates across the active area, the current output for each segment can be used to calculate the position of the spot. A lateral positional sensitive detector includes a single active element in which the photodiode surface resistance is used to determine position. Accurate position information is obtained independent of the light spot intensity profile, symmetry or size. The device response is uniform across the detector aperture, with no dead space.

FIG. 10B is a schematic detail of pump 100 with a meniscus detection arrangement. In one embodiment, imaging system 102 includes mirror 192 on the opposite side of the drip tube to reflect light 182 back through the drip tube and beam splitter 194 to direct the reflected light to sensor 188. This configuration enables placement of all the electronics for the optical components on the same side of the tube.

The following provides further detail regarding meniscus level measurement. The drip chamber remains partially filled with fluid at all times during operation. The air trapped in the drip chamber is in pressure equilibrium with the fluid above and below it. The difference in pressure across the air gap drives fluid out of the bottom of the drip chamber and through downstream tubing 108. Fluid enters and leaves the drip tube chamber continuously as the drop grows in volume, and hence the meniscus level of the fluid remains nearly constant. However, changes in the meniscus level can occur for several reasons: transient changes may occur when a drop detaches and falls into the fluid below; or fluctuations may occur due to pressure oscillations in the fluid (due to pump vibration, motion of the tubing set, or motion of the patient). These transient changes will fluctuate around a mean meniscus value, and hence do not indicate changes in flow rate over times long compared to the characteristic fluctuation times.

Variations that change the mean meniscus level over longer times may occur due to changes in the external pressure environment (e.g., in a traveling vehicle or aircraft), changes in backpressure arising from medical issues with the patient, or due to occlusions or other malfunctions in the pumping process. These long-term meniscus level changes represent a concomitant change in the overall flow rate, and may be used to provide a refinement to the flow measurements described supra. Hence, it may be desired to monitor the level of the meniscus during the infusion, and to use the information derived therein as an indicator of operational problems with the infusion system, or as an adjunct to the primary optical flow measurement.

The method described above for measuring the level of fluid 146 uses the reflection of a light beam from the top surface of the fluid in the drip chamber. The axis of the reflected beam is shifted (deflected) laterally as the fluid level changes, for example, as shown by light 182A and 182B. The amount of deflection depends only on the fluid level change, and on the incident angle of the beam. Although a laser light source is shown in the figure, the technique is compatible with any light beam. Further, although the beam is shown freely propagating, the system may also incorporate lens elements to control the beam.

In one embodiment (not shown), sensor 126 (the imaging focal plane array) is used both for imaging drop 124 and measuring the meniscus of fluid 146 via beam splitters and other simple optics. Sensor 126 can be shared in at least two ways: a portion of the sensor that is not used for pendant drop imaging can simultaneously record the deflected beam; or illumination system 118 for pendant drop imaging and meniscus level measurement can be alternated in time, such that the sensor alternately records the drop image and the deflected beam image. For example, pump 100 can combine the imaging systems 102 shown in FIGS. 2 and 10A/10B or shown in FIGS. 2 and 9A.

Thus, in one embodiment, system 102 includes a first light source, such as light source 172 for transmitting light into the drip tube such that the light reflects off an internally facing surface of the drip tube, and the reflected light is transmitted through the end of the drip tube into an interior of a drop of the IV fluid hanging from the first end of the drip tube. System 102 also includes a second light source, such as light source 188, transmitting light, at an acute angle with respect to a longitudinal axis for the drip chamber, into the drip chamber such that the light reflects, at the acute angle, off a surface for IV fluid disposed within the drip chamber. Optical sensor 126 is for: receiving the reflected light transmitted from the interior of the drop; receiving the reflected light from the second light source; and transmitting, to the computer processor, data regarding the received light from the first and second light sources. The microprocessor is for calculating a volume of the drop using the data regarding the light received from the first light source, and calculating a position of the surface of the using the data regarding the light received from the second light source, as described supra.

Figure 11:
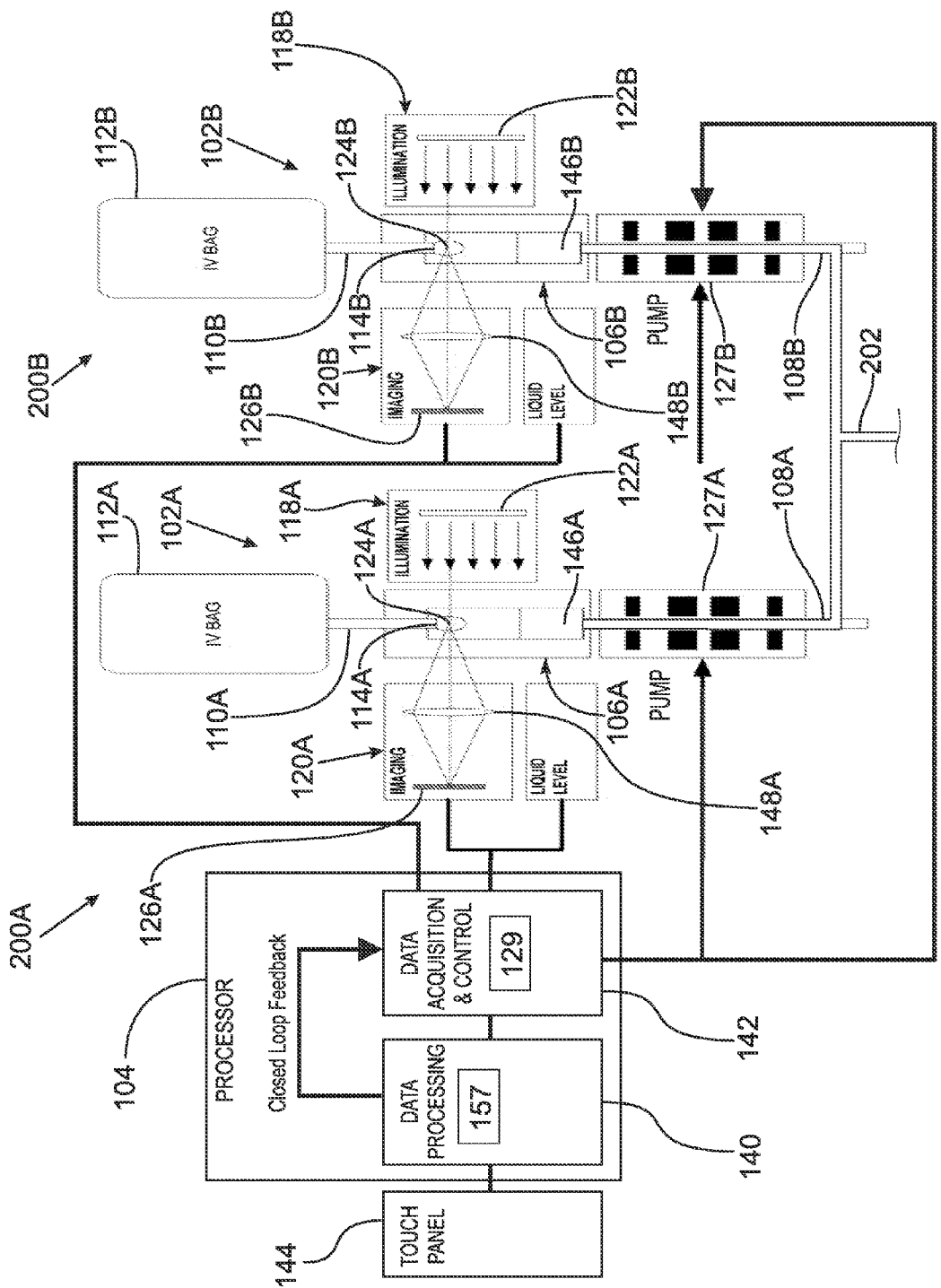
FIG. 11 is a schematic block representation of two infusion pumps with respective optical imaging system in a primary and secondary configuration.

FIG. 11 is a schematic block representation of pump assemblies 200A and 200B with respective optical imaging system in a primary and secondary configuration. The assemblies include the components for pump 100 described supra, with the exception of the processor and control panel. In general, the description above regarding the operation of pump 100 is applicable to the operation of assemblies 200A and 200B. Assembly 200A is connected to primary fluid source 112A. Pump 200B is connected to primary fluid source 112B. Sources 112A and 112B are arranged in a primary/secondary infusion configuration. For example, a primary medication in source 112A is administrated in coordination with a secondary medication in source 112B. As is known in the art, in a primary/secondary configuration, the medication in the secondary source is infused before the medication in the primary source. Tubings 108A and 108B from pump mechanisms 127A and 127B, respectively, are connected to common tubing 202.

In one embodiment, a single processor and control panel, for example, processor 104 and panel 144 are used for assemblies 200A and 200B. The processor operates assembly 200B according to appropriate protocols until the regime for the fluid in source 112B is completed. Then, the processor automatically deactivates assembly 200B as required and begins the infusion of the fluid in source 112A. In one embodiment (not shown), each assembly has a separate processor and control panel or each assembly has a separate processor and a common control panel.

Figure 12:
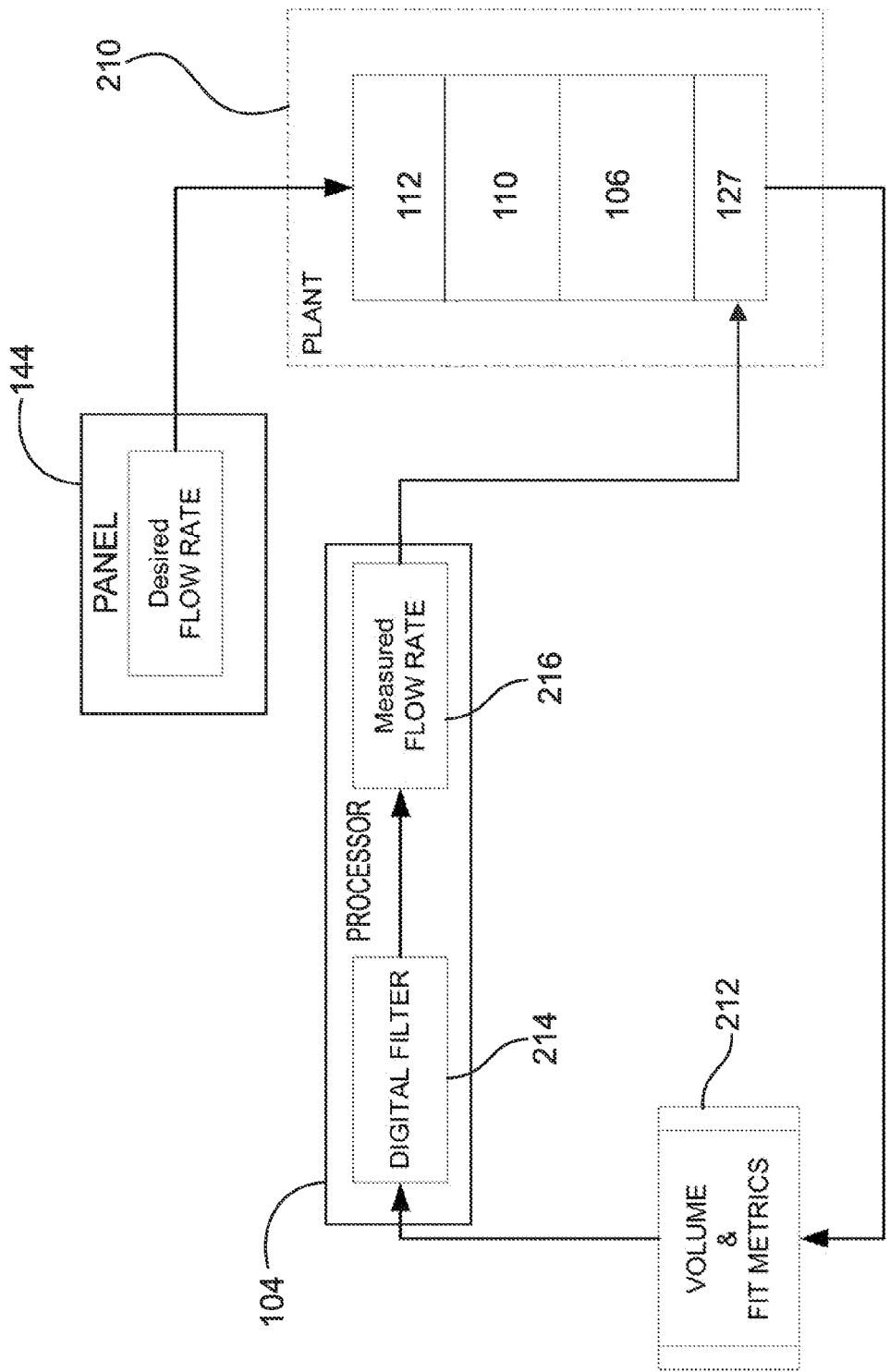
FIG. 12 is a top-level block diagram illustrating operation of a pump with an optical imaging system.

FIG. 12 is a top-level block diagram illustrating operation of pump 100 with an optical imaging system. In one embodiment, the volume measurement, and fit metrics if applicable, described above are fed into a digital signal processing algorithm that calculates the flow rate and provides feedback to the pump control system. Plant 210 includes source 112, the drip chamber, the drip tube, and pump mechanism 127. The microprocessor outputs the Volume and Fit Metrics 212, which are filtered by digital filter 214 in a portion of the microprocessor to provide measured flow rate 216. The measured flow rate is compared with the desired flow rate, for example, input into the microprocessor via panel 144, closing the feedback loop for pump 100.

Figure 13:
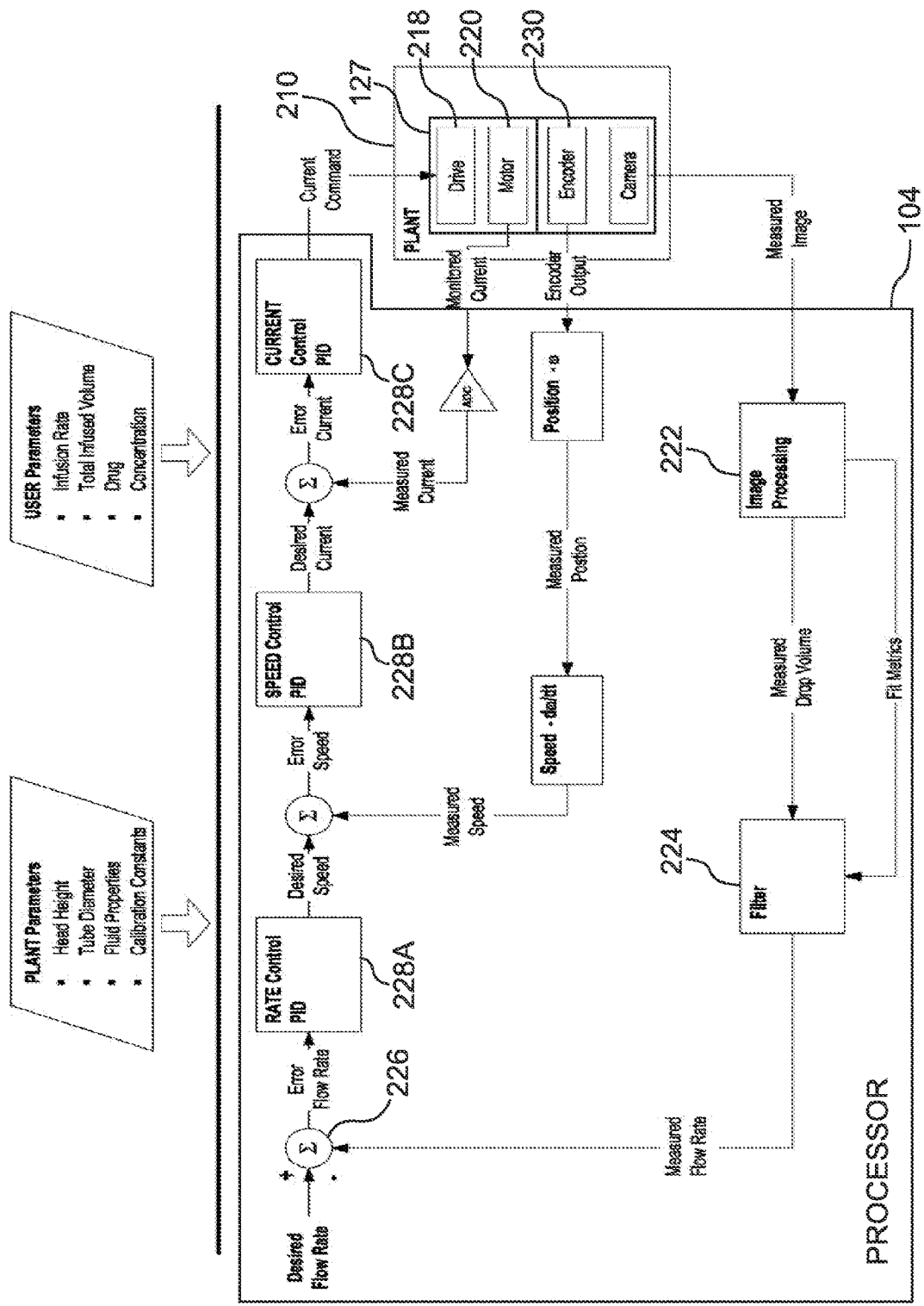
FIG. 13 is a block diagram illustrating example signal processing and feedback control for a pump with an optical imaging system.

FIG. 13 is a block diagram illustrating example signal processing and feedback control for pump 100 with an optical imaging system. Mechanism 127 includes drive 218 and motor 220. Imaging data from system 102 is processed by image processing block 222 to generate a Measured Drop Volume, and the results are input to filter block 224. The output of the filter block is the Measured Flow Rate. The Measured Flow Rate is compared to the Desired Flow Rate by comparator 226, providing the Error Flow Rate (error estimate). The Error Flow Rate feeds into a staged series of PID (Proportional, Integral, Derivative) control algorithms 228. Each PID block operates on a successively faster time scale. Block 228A controls the flow rate, block 228B controls the pump motor speed, and block 228C controls the pump motor current. The speed control incorporates feedback from motor position encoder 230. The current control incorporates feedback from a motor current sensor in motor 220.

Figure 14:
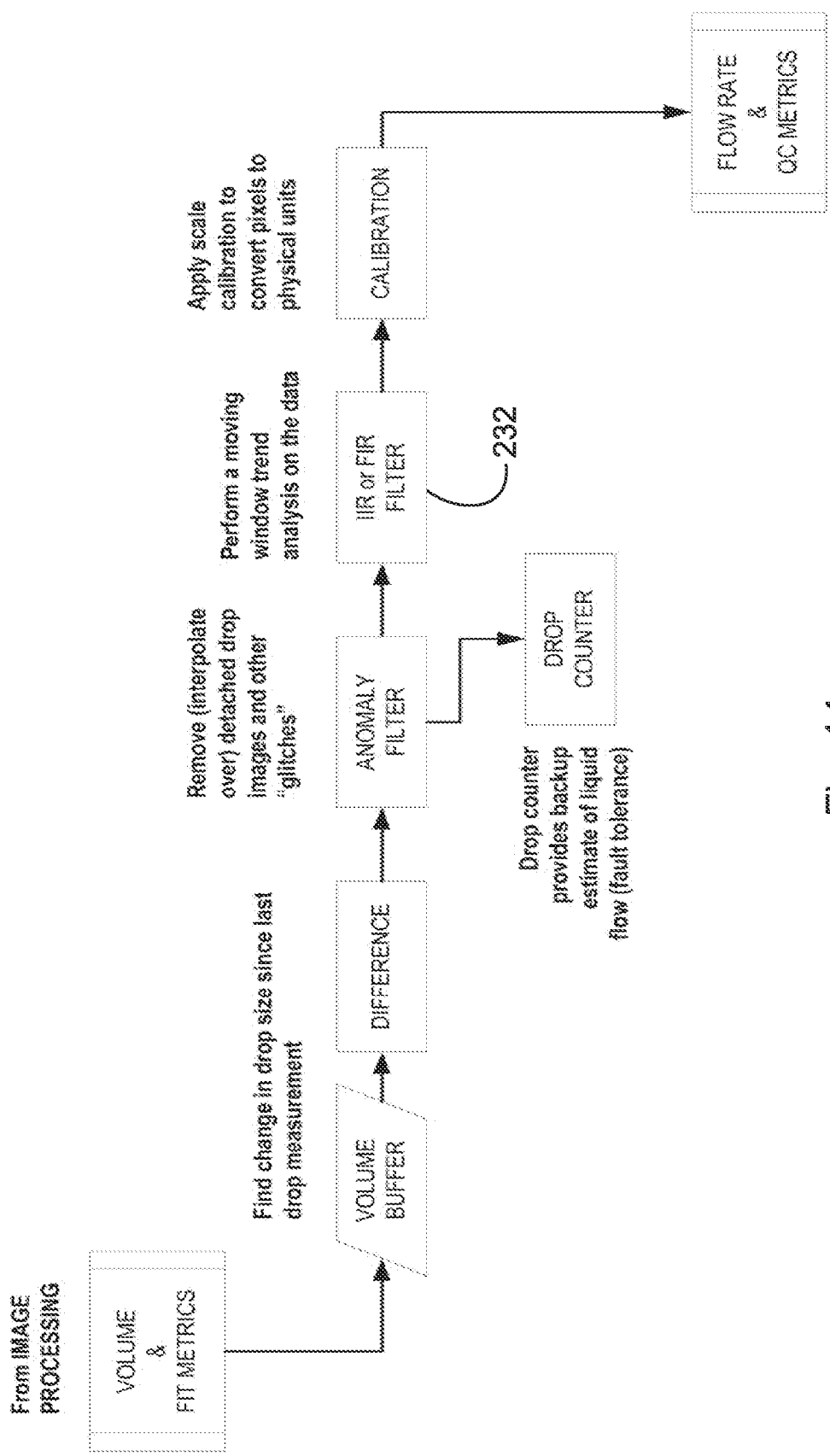
FIG. 14 is a block diagram illustrating example digital filtering in a pump with an optical imaging system.

FIG. 14 is a block diagram illustrating example digital filtering in pump 100 with an optical imaging system. Filter 232 can be any filter known in the art, for example, the general class of FIR/IIR filters known to those skilled in the art. A simple example is an FIR filter that implements a time average over a number of samples.

Figure 15:
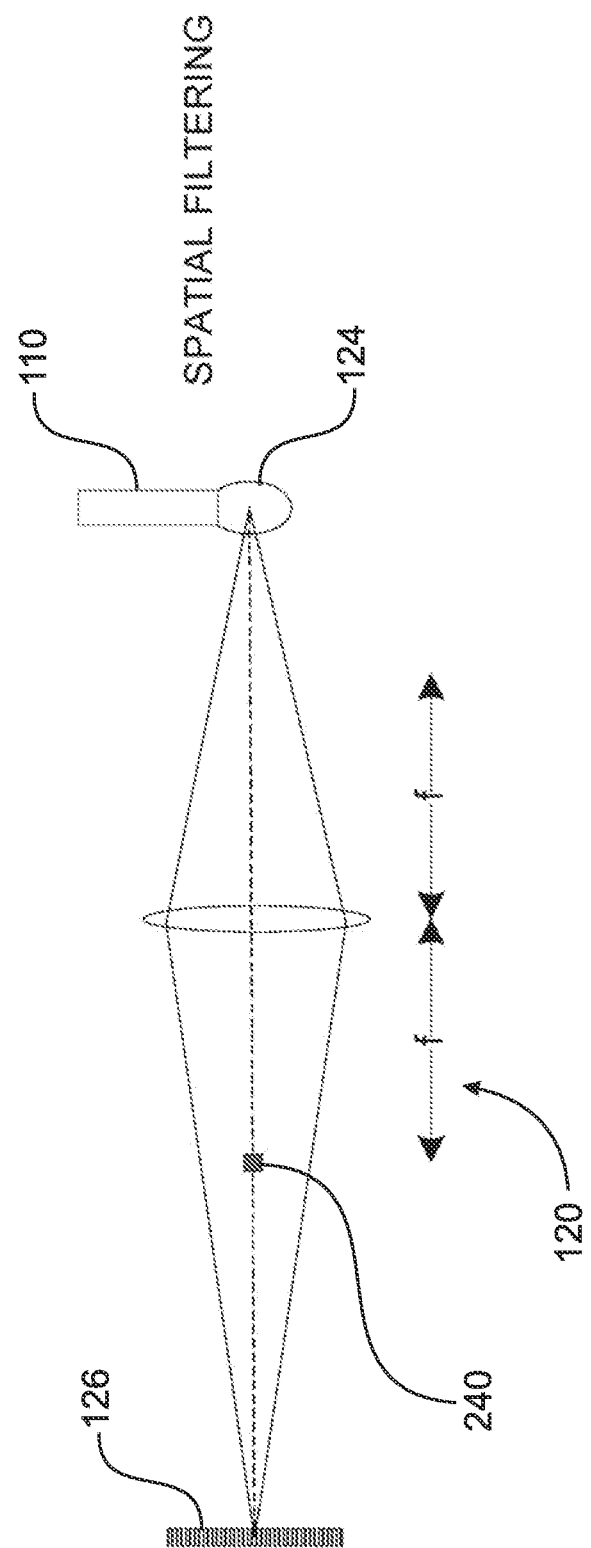
FIG. 15 is a schematic representation of example spatial filtering in a pump with an optical imaging system.

FIG. 15 is a schematic representation of example spatial filtering in pump 100 with an optical imaging system. The goal of high resolution and edge definition for images of drop 124 are attained by illumination techniques, optical techniques, or both, for example, as described supra. In one embodiment, spatial filtering techniques are used in the optics for system 120. For example, mask 240 at the back focal plane of imaging system 102 modifies (via optical Fourier transform) the image generated by the optical system, for example, sensor 126. A DC block filter is shown in FIG. 15. This filter blocks the central cone of the transmitted light and enhances edge images (associated with scattered light).

In one embodiment, the sensitivity of sensor 126 is matched to the illumination spectrum of the light source in system 118. In one embodiment, sensor 126 is a low-cost visible light sensor (400-1000 nm wavelength) and source 122 generates light that is outside the range of human visual perception (i.e., 800-1000 nm). In this case the operator will not be distracted by the bright illumination source.

It should be understood that pump 100 can be any pump mechanism or pump application known in the art and is not limited to only IV infusion pump applications. In the case of a gravity-fed system, the pumping mechanism can be replaced by a valve or flow restrictor, and still be compatible with the configurations and operations described supra.

Figure 16:
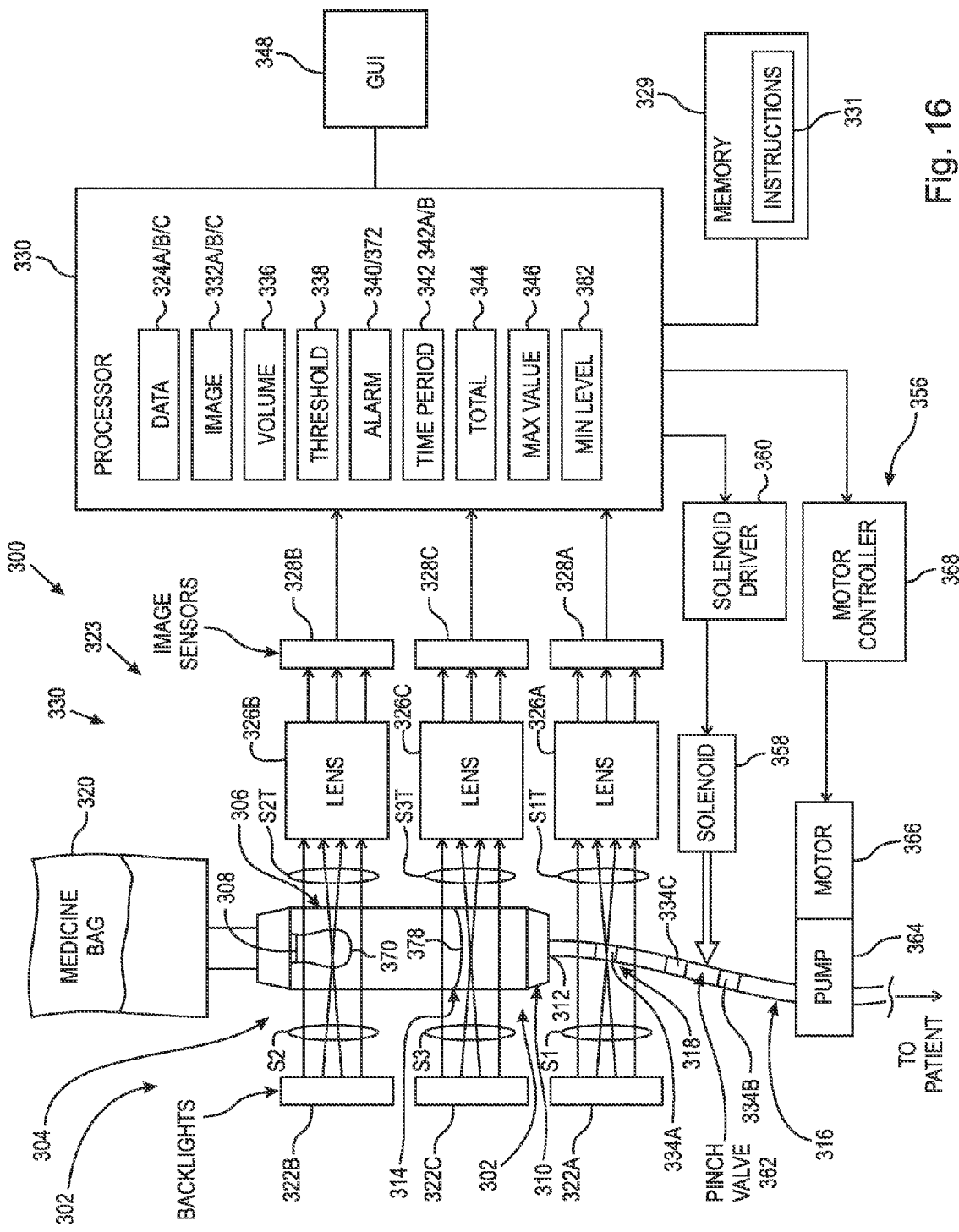
FIG. 16 is a schematic representation of an optical imaging system.

FIG. 16 is a schematic representation of optical imaging system 300. In an example embodiment, system 300 is used with infusion tube 302 including drip chamber 304. Drip chamber 304 includes portion 306 with drip tube 308, portion 310 including exit port 312, and portion 314 between portions 306 and 310. Output tube 316 can be connected to exit port 312 and includes portion 318. Output tube 316 is connected to exit port 312 and is for flowing the fluid out of drip chamber 304. Drip tube 308 is for connection to source of fluid 320, for example, medication bag 320. System 300 includes source 322A for emitting light S1. System 300 includes optical system 323.

Light source 322A can be any light source known in the art, including, but not limited to a light-emitting diode (LED), an array of LEDs, a laser diode, an incandescent lamp, or a fluorescent lamp.

Optical system 323 receives light S1T, including light S1 emitted by source 322A and transmitted by portion 318 or 310, and transmits data 324A characterizing S1T. In an example embodiment, optical system 323 includes lens 326A for receiving and transmitting light S1T transmitted through portion 318 or portion 310. In FIG. 16, S1 is transmitted through portion 318; however, it should be understood that S1 can be transmitted through exit port 312 as well, in particular, the portion of exit port 312 to which output tube 316 is secured. In an example embodiment, optical system 323 includes image sensor 328A for receiving S1T from lens 326A. Sensor 328A generates and transmits data 324A characterizing S1T received by lens 326A. System 300 includes memory element 329 and at least one processor 330. Memory element 329 is configured to store computer executable instructions 331 and processor 330 is configured to execute instructions 331 to generate, using data 324A, image 332A of output tube 316.

By "characterize" we mean that the respective data describes, or quantifies, the spectrum of light, for example, providing parameters enabling generation of an image using the respective data. By "emitting light" we mean that the element in questions generates the light. By "transmitted by" we mean passing light through the element in question, for example, light emitted by light source 322A passes through portion 318.

Processor 330 is configured to execute instructions 331 to detect, using image 332A, air bubble 334 in portion 318 or 310. For a detected air bubble 334, processor 330 is configured to execute instructions 331 to determine volume 336 of air bubble 334, compare volume 336 to threshold value 338, and for volume 336 exceeding threshold value 338, generate and transmit air alarm signal 340 indicating an air-in-line condition.

In an example embodiment, processor 330 is configured to execute instructions 331 to detect, during predetermined time period 342A, a plurality of air bubbles 334 sequentially passing through portion 318 or 310. By "sequentially passing" we mean that the bubbles pass through portion 318 or 310 in a sequence separated by respective time intervals. For example, processor 330 detects, in sequence, bubble 334B, then bubble 334C after a time interval, and then air bubble 334A after another time interval as bubbles 334A/B/C pass through portion 318 or 310. Processor 330 is configured to execute instructions 331 to determine a respective volume 336 for each air bubble 334 in the plurality of air bubbles 334 as each air bubble 334 is detected, and calculate running total 344 of respective volumes 336 as respective volumes 336 are determined.

In an example embodiment, air bubble 334A is a final, or last, air bubble in the sequence for the plurality of air bubbles 334. By "final, or last, air bubble" we mean the most recently detected air bubble 334 in a sequence of air bubble 334, separated by respective time intervals, passing through portion 318 or 310. In this example, threshold value 338 is a value for respective volume 334 for the last air bubble 334 that increases running total 344 beyond predetermined maximum value 346. In an example embodiment, threshold value 338 is a maximum allowable volume for running total 344 and processor 330 is configured to generate and send air alarm signal 340 when running total 344 exceeds maximum value 346.

As is known in the art, in some instances, a certain amount of air present in the fluid passing through output tube 316 over a specified time period is acceptable. However, the air in the fluid becomes an air-in-line condition if the cumulative volume for the air (running total 344) exceeds a certain amount during the specified time period (time period 342A). Thus, pump 300 determines a maximum volume of air (value 346) that is permissible in output tube 316 for specified time period 342. When an air bubble 334 detected during the time period causes the total volume of air passing through output tube 316 during time period 342 to exceed the maximum value 346, which is an unsafe air-in-line condition, processor 330 generates and transmits alarm signal 340.

In an example embodiment, threshold value 338 is a predetermined maximum value for a single air bubble 334. Thus, processor 330 generates and transmits air alarm signal 340 when an air bubble 334 with a volume greater than the predetermined maximum value is detected. Note that the predetermined maximum value for a single air bubble 334 can be less than predetermined maximum value 346 for running total 344.

In an example embodiment, pump 300 includes graphical user interface (GUI) 348. GUI 348 is configured to graphically and/or audibly express alarm 340. In an example embodiment, GUI 348 is configured to graphically and/or audibly express some or all of volume 336, threshold 338, total 344, and maximum value 346. Advantageously, the respective expressions enable medical practitioners to monitor possible air-in-line conditions and detect trends, for example, a rapidly incrementing total 346, to anticipate problems and take proactive action.

Figure 17:
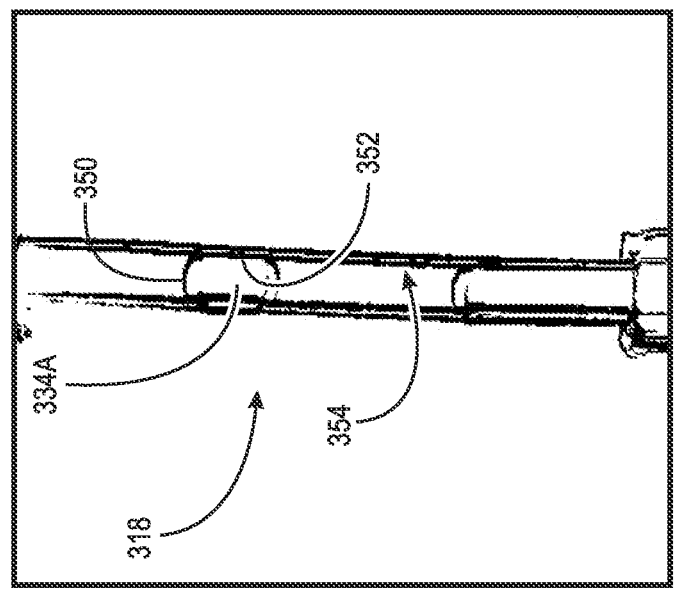
FIG. 17 is a pictorial representation of a binary image of an air bubble in an output tube.

FIG. 17 is an illustrative pictorial representation of a binary image of an air bubble in an output tube. Processor 330 is configured to execute instructions 331 to identify, using image 332A, and respective boundaries 350 of air bubble 334A. As described supra, in an example embodiment, processor 330 is configured to execute instructions 331 to fit a parametric function to boundaries 350 and integrate the parametric function to obtain volume 336. In an example embodiment, boundaries 350 include boundaries 352 of interior surfaces 354 of portion 318 of output tube 316. In an example embodiment as described supra, processor 330 is configured to execute instructions 331 to use boundary 352 of the interior surfaces of the portion 318 or 310 as a reference plane for calculating a volume, shape, or location of air bubble 334A. The widths of boundaries 350 and 352 have been exaggerated in FIG. 17 for purposes of illustration. The smallest width of an edge available from a black and white image is about the width of a pixel. In actual practice, processor 330 is configured to execute instructions 331 to localize the respective widths of the respective edges of boundaries 350 and 352 to about $1/10^{th}$ the width of a pixel.

In an example embodiment, image 332A is initially a grayscale image. By grayscale or greyscale image we mean an image in which the value of each pixel is a single sample, that is, it carries only intensity information. Images of this sort, also known as black-and-white, are composed exclusively of shades of gray, varying from black at the weakest intensity to white at the strongest. Grayscale images are distinct from one-bit bi-tonal black-and-white images, which in the context of computer imaging are images with only the two colors, black, and white (also called bilevel or binary images). Grayscale images have many shades of gray in between. Grayscale images are also called monochromatic, denoting the presence of only one (mono) color (chrome). As noted supra, boundaries between areas of interest can be difficult to discern in a grayscale image, for example, in the case when intensities are not particularly divergent at the boundaries. Advantageously, in an example embodiment, processor 330 is configured to compute, as described supra, binary image 332A, as shown in FIG. 17, including boundaries 350 and 352. Advantageously, boundaries 350 and 352 in the binary image are more clearly defined than in a grayscale image, enabling greater accuracy in the detection and volume determination of air bubbles 334 in portion 318 or 310.

In an example embodiment, pump 300 includes mechanism 356 for controlling flow to drip chamber 304 or from drip chamber 304 and processor 330 is configured to execute instructions 331 to operate mechanism 356 to shut off flow to or from drip chamber 304 when air alarm signal 340 is generated. In an example embodiment, mechanism 356 includes solenoid 358, solenoid driver 360, and pinch valve 362. Processor 330 energizes driver 360 to activate solenoid 358 to displace pinch valve 362 to shut off flow through output tube 316. In an example embodiment, mechanism 356 includes pump 364, motor 366, and motor controller 368. Processor 330 sends control signals to controller 368 to operate motor 366 such that pump 364 blocks flow through output tube 316. In an example embodiment (not shown), pinch valve 362 is engaged with drip tube 308 between bag 320 and drip chamber 304.

In an example embodiment, optical system 324 receives light S2T, including light S2 emitted by source 322B and transmitted by portion 306, and transmits data 324B characterizing S2T. In an example embodiment, optical system 323 includes lens 326B for receiving light S2T transmitted by portion 306 and image sensor 328B. Image sensor 328B transmits to processor 330, data 324B regarding the light received from lens 326B. Processor 330 is configured to execute instructions 331 to generate, using data 324B, a plurality of successive images 332B of portion 306 during a predetermined time period 342B. Processor 330 is configured to execute instructions 331 to determine, using images 332B an absence of drop 370, pendant from the end of drip tube 308, during time period 342B and generate and transmit empty bag alarm signal 372 indicating that the source 320 of fluid is empty.

Figure 18:
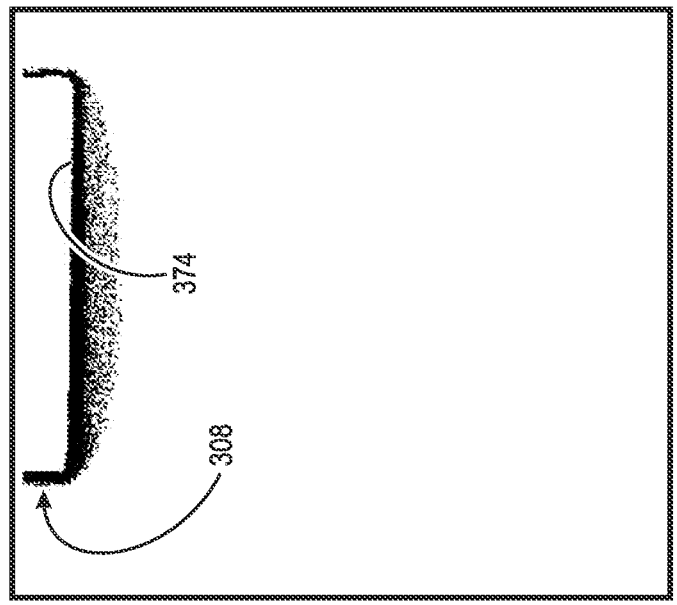
FIG. 18 is a pictorial representation of a binary image of an end of a drip tube in a drip chamber.

FIG. 18 is a pictorial representation of a binary image of an end of a drip tube in a drip chamber. In an example embodiment, image 332B is initially a grayscale image. Advantageously, in an example embodiment, the processor is configured to compute, as described supra, binary image 332B, as shown in FIG. 18, including boundary 374 for an end of drip tube 308. Advantageously, boundary 374 in the binary image is more clearly defined than in a grayscale image, enabling greater accuracy in the detection of pendant drop 370 or a lack of pendant drop 370 at the end of drip tube 308. In an example embodiment, as described supra, processor 330 is configured to execute instructions 331 to use boundary 374 as a reference plane for calculating a presence or absence of pendant drop 370 at the end of drip tube 308.

In an example embodiment, optical system 324 receives light S3T, including light S3 emitted by source 322C and transmitted by portion 314, and transmits data 324C characterizing S3T. In an example embodiment, optical system 323 includes lens 326C arranged to receive the light from backlight 322C transmitted by portion 314 and image sensor 328C arranged to receive the light focused by lens 326C. Sensor 328C transmits data 324C, to the processor. Processor 330 is configured to execute instructions 331 to generate, using data 324C, image 332C of portion 314. Processor 330 is configured to execute instructions 331 to determine, using image 332C an absence of fluid in portion 314 and generate and transmit air alarm 340 or empty bag alarm signal 372.

Figure 19:
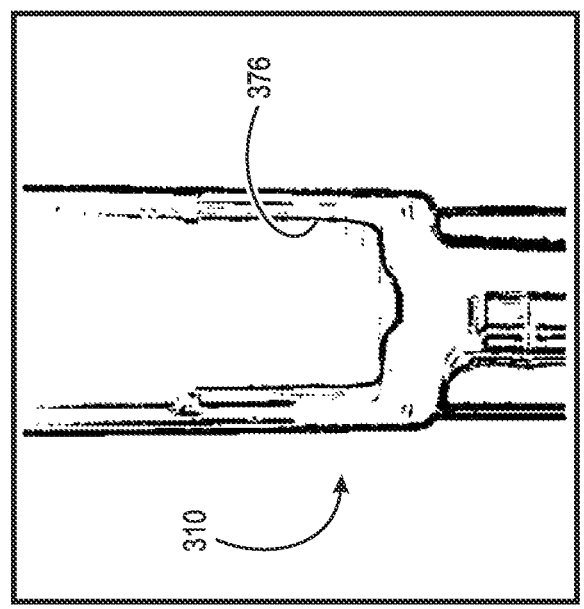
FIG. 19 is a pictorial representation of a binary image of an end of a drip chamber including an exit port; and, FIG. 20 is a pictorial representation of a binary image of a meniscus in a drip chamber.

FIG. 19 is a pictorial representation of a binary image of an end of a drip chamber including an exit port. In an example embodiment, image 332C is initially a grayscale image. Advantageously, in an example embodiment, processor 330 is configured to compute as described supra, binary image 332C, as shown in FIG. 19, including boundary 376 for portion 310. Advantageously, boundary 376 in the binary image is more clearly defined enabling greater accuracy in the detection of a lack of a fluid in portion 310. In an example embodiment, as described supra, processor 330 is configured to use boundary 376 as a reference plane for calculating the absence of fluid in portion 310.

In an example embodiment, processor 330 is configured to execute instructions 331 to determine, using image 332A, that portion 318 of output tube 316 is free of an air bubble while at the same time determining the absence of fluid in portion 314 of drip chamber 304. The lack of fluid in portion 314 will eventually result in air in output tube 316. Processor 330 is configured to execute instructions 331 to generate and transmit air alarm signal 340 in response to the two preceding conditions. Thus, system 300 is able to anticipate an air-in-line condition before the condition actually manifests. Advantageously, system 300 is able to send alarm 340 before air in drip chamber 304 passes into output tube 316, enabling a quicker and more proactive response by medical practitioners and reducing the risk of a detrimental air-in-line condition.

Figure 20:
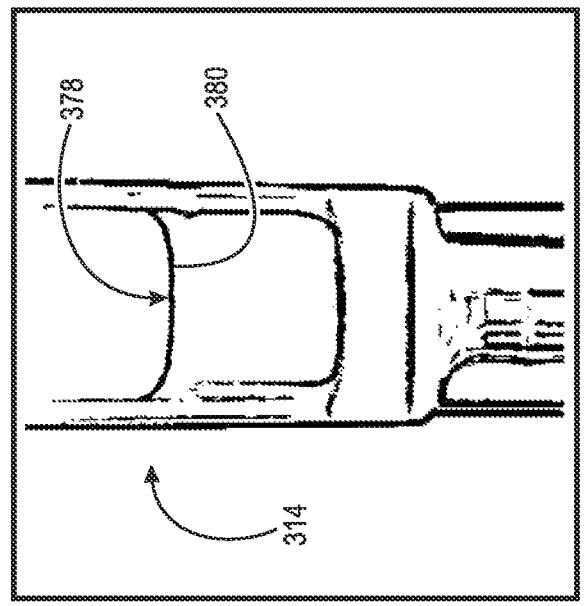

FIG. 20 is a pictorial representation of a binary image of meniscus 378 in portion 314 of drip chamber 304. In an example embodiment, processor 330 is configured to use binary image 332C to identify boundary 380 for meniscus 378 in portion 314 and determine, using boundary 380, that the fluid in portion 314 is below minimum level 382. In an example embodiment, image 332C is initially a grayscale image. Advantageously, in an example embodiment, processor 330 is configured to compute as described supra, binary image 332C, as shown in FIG. 20, including boundary 380 for meniscus 378. Advantageously, boundary 380 in the binary image is more clearly defined enabling greater accuracy in the determination of the level of meniscus 378. In an example embodiment, processor 330 is arranged to execute instructions 331 to generate and transmit empty bag alarm signal 372 in response to detecting the fluid in portion 314 below minimum level 382. That is, if source 320 of fluid is continuing to supply fluid to drip chamber 304, the fluid is expected to remain above minimum level 382. However, when source 320 of fluid is exhausted, fluid no longer flows into drip chamber 304 and continued flow through output tube 316 results in the level of meniscus 378 decreasing. Once the level reaches minimum level 382, it can be inferred that the reduction in level is not part of ordinary fluctuation during an infusion regimen, but rather is due to bag 320 being empty or occluded.

In an example embodiment, as described supra, processor 330 is configured to execute instructions 331 to use a portion of boundary 380, for example, 380A, as a reference plane for determine that the fluid in portion 314 is below minimum level 382. The crisper and more easily differentiated boundary of meniscus 378 in the binary image enables more accurate and precise measurement of the level of fluid in drip chamber 304, which in turn results in more accurate assessment of and recognition of an empty bag condition. In an example embodiment, the measurement of the level of meniscus 378 is used as a control parameter for operating pump 364.

Processor(s) 330 can be any one or more processors or microprocessors known in the art. Lenses 326A/B/C and sensors 328A/B/C can be any lenses and sensors known in the art. In an example embodiment, sensors 328A/B/C are black and white image sensors. In an example embodiment (not shown) a single backlight emits light transmitted by portions 306, 310, 314, and 318.

The following is applicable to FIGS. 17 through 20. In an example embodiment, subpixel edge localization is used to define an air bubble, a drip tube, a portion of a drip chamber including an exit port, and/or a meniscus. In most machine vision systems in which an electronic image is being processed, the fundamental structure being identified and manipulated within the image is the edge. Edges are used in computer vision to demarcate where one object ends and another begins, intersections between objects, and to determine the size of an object. Edges can be straight lines, curved arcs, or closed to form circles or squares, for example. Furthermore, an edge can be broad and occur over several pixels, or narrow such that it is only one pixel wide.

An edge is seen, both by humans and within computer vision systems, where the gradient of the intensity changes within the image. For example, if an image contains a white ball within a dark background, the edge of the ball is discerned to be where the dark background pixels meet the white pixels of the ball. Three observations can be made about this simplistic image: 1) the two-tone purely black and white image can only provide coarse information about the actual location of the edge of the ball, being limited by the size of the pixel, 2) most images have gray scale pixel values in which the number of shades of gray available for processing is at least 256, and more typically 1024, or even 4096, and 3) due to the non-ideal imaging capabilities of the lens and image sensor capturing the image, the transition from white to dark across an edge generally does not occur at a single pixel but over several pixels. The additional gray-scale information across several pixels comprising an edge allows for finer edge localizing, at scales significantly less than the width of a pixel, which is known in the art as subpixel edge localizing.

The need for subpixel edge localizing occurs frequently in machine vision applications where the exact location of an object is needed, so, for example, a robotic arm can reach out and grasp the object (at its edges). A second use for subpixel edge localizing occurs in metrology machine vision applications where the length, area, or even volume of an object needs to be measured and computed with a high degree of accuracy. If, for example, the aforementioned ball is nominally 10 mm in diameter, and its actual diameter must be measured to 40 μm (0.04 millimeter) accuracy. Also, if the imaging system has been previously calibrated, and its magnification is known to be exactly 10 pixels per millimeter (or equivalently, 0.1 millimeter/pixel), then the diameter of the ball is nominally 100 pixels across, and each of its two opposing edges must be localized to 20 μm so that their sum is less than or equal to the 40 μm measurement tolerance. Note that 20 μm of object distance corresponds to ⅕ the width of a pixel in this example, and subpixel edge localizing is required.

One subpixel edge localizing algorithm determines the average brightness of the object on one side of the edge, I1, then finds the average brightness on the other side of the edge, I2, and then interpolates between intensity values of the pixels across the edge to find the subpixel location corresponding to the half-intensity point, (I1+I2)/2. However, the results of this algorithm, like any two-point interpolation algorithm, are strongly limited by noise present in the pixels.

To limit the effects of noise, many edge-localizing algorithms attempt to fit the central portion of the edge's intensity profile to a line using a linear regression formula. Once the formula for this line is known it is a simple matter to plug in the known half-intensity point (I1+I2)/2 and solve for the subpixel location. Note that the regression can occur over between three and fifteen or more pixels, and the noise effects of any one pixel on localization accuracy are greatly reduced.

The regression algorithm can be carried a step further in which the linear fit is replaced with a fit to the Error Function (most classical unaberrated blur functions have this profile), or even a fit to a polynomial which can account for nonlinear edge profiles, and it can be expanded to include pixels that are not near the central portion of the edge. For example, if a third order polynomial is used, being of the form Pixel Location=$P=A+BI+CI^2+DI^3$, and the coefficients A, B, C, and D are determined with non-linear regression, then the point of inflection (i.e., the location of the edge) is known to be at $I=-C/3D$. This value of I (and the coefficients) is then plugged back into the equation for P and the sub-pixel edge location is determined.

The process to localize an edge with subpixel accuracy is to:

1) Locate the coarse location of the edge, to the nearest pixel. This is commonly done in the art by using the Canny edge finding algorithm.

2) For each row of pixels containing an edge, select the pixels (usually based on gradient) that are to be part of the regression, for each edge in the row.

3) Apply the regression to the selected pixels, and fit the edge intensity profile to a given mathematical expression.

4) Find the subpixel edge location by using the regressed mathematical expression.

Thus, it is seen that the objects of the invention are efficiently obtained, although changes and modifications to the invention should be readily apparent to those having ordinary skill in the art, without departing from the spirit or scope of the invention as claimed. Although the invention is described by reference to a specific preferred embodiment, it is clear that variations can be made without departing from the scope or spirit of the invention as claimed.

What is claimed is:

1. An optical imaging system for use with an infusion tube having a drip chamber and an output tube, wherein the drip chamber includes a first portion with a drip tube, a second portion with an exit port, and a third portion located between the first and second portions, the optical imaging system comprising:
   an illumination system with at least one light source for emitting first light;
   an optical system for:
   receiving the first light transmitted by the output tube or the second portion; and,
   transmitting first data characterizing the received first light;
   a memory element configured for storing computer executable instructions; and,
   at least one processor configured for executing the computer executable instructions to:
   detect, using the first data, an air bubble in the output tube or the second portion;
   determine a volume of the detected air bubble;
   identify a peripheral edge shape of a drop pendant from an end of the drip tube for detecting the air bubble;
   determine a volume of the drop pendant based on outer surface information of the drop having three dimensional coordinates, wherein the volume of the drop is determined based on
   a fit-constrained image of the drop representing an entire outer boundary of the drop using a fitting algorithm based on the peripheral edge shape of the drop, wherein the volume of the drop is determined by fitting a parametric function to the entire outer boundary of the drop and integrating the parametric function against the drop having rotational symmetry.

2. The optical imaging system of claim 1, wherein the at least one processor configured for executing the computer executable instructions to:
  compare the volume to a threshold value; and,
  for a volume exceeding the threshold value, generate and transmit an air alarm signal.

3. The optical imaging system of claim 1, wherein:
  detecting an air bubble in the output tube or the second portion includes detecting, during a predetermined time period, a plurality of air bubbles sequentially passing through the output tube or the second portion;
  determining a volume of the detected air bubble includes determining a respective volume for each air bubble in the plurality of air bubbles as said each air bubble is detected; and,
  determining a volume of the detected air bubble includes calculating a running total of the respective volumes as the respective volumes are determined.

4. The optical imaging system of claim 3, wherein the at least one processor configured for executing the computer executable instructions to:
  determine that the respective volume for a last air bubble passing in sequence through the output tube or the second portion increases the running total beyond a predetermined maximum value; and,
  generate and transmit an air alarm signal.

5. The optical imaging system of claim 3, wherein the at least one processor configured for executing the computer executable instructions to:
  compare the running total to a threshold value; and,
  for a running total exceeding the threshold value, generate and transmit an air alarm signal.

6. The optical imaging system of claim 2, wherein the threshold value includes a predetermined maximum value for a single air bubble.

7. The optical imaging system of claim 1, wherein:
  the at least one processor is configured for executing the computer executable instructions to identify, using the first data, respective boundaries of the air bubble; and,
  determining the volume of the air bubble includes:
  fitting the parametric function to the respective boundaries of the air bubble; and,
  integrating the parametric function to obtain the volume of the air bubble.

8. The optical imaging system of claim 1, wherein:
  the at least one light source is configured for emitting second light;
  the optical system is configured for:
  receiving the second light transmitted by the first portion of the drip chamber; and,
  transmitting, to the at least one processor, second data characterizing the received second light; and,
  the at least one processor configured for executing the computer executable instructions to:
  generate, using the second data, a plurality of successive images of the first portion of the drip chamber, during a predetermined time period;
  determine, using the plurality of successive images, an absence of the drop pendant from the end of the drip tube, during the predetermined time period; and,
  generate and transmit an empty bag alarm signal.

9. The optical imaging system of claim 8, wherein the at least one processor configured for executing the computer executable instructions to:
  generating an image of the end of the drip tube;
  identify, using the image, a boundary of the end of the drip tube; and,
  use the boundary as at least one reference plane for determining the absence of the drop.

10. The optical imaging system of claim 1, wherein:
  the at least one light source is configured for emitting third light;
  the optical system is configured for:
  receiving the third light transmitted by a third portion of the drip chamber; and,
  transmitting, to the at least one processor, third data characterizing the received third light; and,
  the at least one processor configured for executing the computer executable instructions to:
  create an image of the third portion of the drip chamber;
  determine, using the image:
  an absence of fluid in the third portion of the drip chamber; or,
  a fluid level in the third portion below a predetermined level; and,
  generate and transmit an empty bag alarm or the air alarm signal.

11. The optical imaging system of claim 1, wherein:
  the at least one light source consists of a single light source; or, the at least one light source consists of three light sources.

12. A method of imaging an infusion tube having a drip chamber and an output tube, wherein the drip chamber includes a first portion with a drip tube, a second portion with an exit port, and a third portion located between the first and second portions, comprising:
  storing computer readable instructions in a memory element;
  emitting first light from at least one light source;
  receiving, using an optical system, the first light transmitted by the output tube or the second portion;
  transmitting, using the optical system, first data characterizing the received first light; and,
  executing, using at least one processor, the computer executable instructions to:
  detect, using the first data, an air bubble in the output tube or the second portion;
  determine a three-dimensional volume of the detected air bubble;
  identify a peripheral edge shape of a drop pendant from an end of the drip tube for detecting the air bubble;
  determine a three-dimensional volume of a drop pendant based on
  a fit-constrained image of the drop representing an entire outer boundary of the drop using a fitting algorithm based on the peripheral edge shape of the drop including at least one circle defining the entire outer boundary of the drop, wherein the volume of the drop is determined by fitting a parametric function to the entire outer boundary of the drop and integrating the parametric function against the drop having rotational symmetry.

13. The method of claim 12, further comprising executing, using the at least one processor, the computer executable instructions to:
  compare the volume to a threshold value; and,
  for a volume exceeding the threshold value, generate and transmit an air alarm signal.

14. The method of claim 12, wherein:
  detecting an air bubble in the output tube or the second portion includes detecting, during a predetermined time period, a plurality of air bubbles sequentially passing through the output tube or the second portion;

determining a volume of the detected air bubble includes
determining a respective volume for each air bubble in
the plurality of air bubbles as said each air bubble is
detected; and,
determining a volume of the detected air bubble includes
calculating a running total of the respective volumes as
the respective volumes are determined.

15. The method of claim 14, further comprising executing, using the at least one processor, the computer executable instructions to:
determine that the respective volume for a last air bubble passing in sequence through the output tube or the second portion increases the running total beyond a predetermined maximum value; and,
generate and transmit an air alarm signal.

16. The method of claim 14, further comprising executing, using the at least one processor, the computer executable instructions to:
compare the running total to a threshold value; and,
for a running total exceeding the threshold value, generate and transmit an air alarm signal.

17. The method of claim 13, wherein the threshold value includes a predetermined maximum value for a single air bubble.

18. The method of claim 12, further comprising executing, using the at least one processor, the computer executable instructions to identify, using the first data, respective boundaries of the air bubble; and, wherein:
determining the volume of the air bubble includes:
fitting the parametric function to the respective boundaries of the air bubble; and,
integrating the parametric function to obtain the volume of the air bubble.

19. The method of claim 12, wherein:
the at least one light source is configured for emitting second light; and,
the optical system is configured for:
receiving the second light transmitted by the first portion of the drip chamber; and,
transmitting, to the at least one processor, second data characterizing the received second light; and,
the method further comprising executing, using the at least one processor, the computer executable instructions to:
generate, using the second data, a plurality of successive Images of the first portion of the drip chamber, during a predetermined time period;
determine, using the plurality of successive images, an absence of the drop pendant from the end of the drip tube, during the predetermined time period; and,
generate and transmit an empty bag alarm signal.

20. The method of claim 19, further comprising executing, using the at least one processor, the computer executable instructions to:
generating an image of the end of the drip tube;
identify, using the image, a boundary of the end of the drip tube; and,
use the boundary as at least one reference plane for determining the absence of the drop.

21. The method of claim 12, wherein:
the at least one light source is configured for emitting third light; and,
the optical system is configured for:
receiving the third light transmitted by the third portion of the drip chamber; and,
transmitting, to the at least one processor, third data characterizing the received third light; and,
the method further comprising executing, using the at least one processor, the computer executable instructions to:
create an image of the third portion of the drip chamber;
determine, using the image:
an absence of fluid in the third portion of the drip chamber; or,
a fluid level in the third portion below a predetermined level; and,
generate and transmit an empty bag alarm or the air alarm signal.

22. The method of claim 12, wherein:
the at least one light source consists of a single light source; or,
the at least one light source consists of three light sources.

23. The optical imaging system of claim 1, wherein each horizontal row of the pixel data is integrated from one end of the drop to an opposite end of the drop by summing a volume of each said row.

24. An optical imaging system for use with an infusion tube having a drip chamber and an output tube, wherein the drip chamber includes a first portion with a drip tube, a second portion with an exit port, and a third portion located between the first and second portions, the optical imaging system comprising:
an illumination system with at least one light source for emitting first light;
an optical system for:
receiving the first light transmitted by the output tube or the second portion; and,
transmitting first data characterizing the received first light;
a memory element configured for storing computer executable instructions; and,
at least one processor configured for executing the computer executable instructions to:
detect, using the first data, an air bubble in the output tube or the second portion;
determine a volume of the detected air bubble;
identify a peripheral edge shape of a drop pendant from an end of the drip tube for detecting the air bubble;
determine a volume of the drop pendant based on outer surface information of the drop having three dimensional coordinates, wherein the volume of the drop is determined based on at least one of:
a boundary-constrained image of the drop having pixel data representing actual entire outer left and right boundaries of the drop, and
a fit-constrained image of the drop representing an entire outer boundary of the drop using a fitting algorithm based on the peripheral edge shape of the drop,
wherein the boundary-constrained image of the drop and the fit-constrained image of the drop are compared for estimating the peripheral shape of the drop.

25. An optical imaging system for use with an infusion tube having a drip chamber and an output tube, wherein the drip chamber includes a first portion with a drip tube, a second portion with an exit port, and a third portion located between the first and second portions, the optical imaging system comprising:
an illumination system with at least one light source for emitting first light;
an optical system for:
receiving the first light transmitted by the output tube or the second portion; and,
transmitting first data characterizing the received first light;
a memory element configured for storing computer executable instructions; and, at least one processor configured for executing the computer executable instructions to:

detect, using the first data, an air bubble in the output tube or the second portion;

determine a volume of the detected air bubble;

identify a peripheral edge shape of a drop pendant from an end of the drip tube for detecting the air bubble;

determine a volume of the drop pendant based on outer surface information of the drop having three dimensional coordinates, wherein the volume of the drop is determined based on at least one of:

a boundary-constrained image of the drop having pixel data representing actual entire outer left and right boundaries of the drop, and a fit-constrained image of the drop representing an entire outer boundary of the drop using a fitting algorithm based on the peripheral edge shape of the drop, wherein:

the at least one light source is configured for emitting second light;

the optical system is configured for:

receiving the second light transmitted by the first portion of the drip chamber; and, transmitting, to the at least one processor, second data characterizing the received second light; and, the at least one processor configured for executing the computer executable instructions to:

generate, using the second data, a plurality of successive images of the first portion of the drip chamber, during a predetermined time period;

determine, using the plurality of successive images, an absence of the drop pendant from the end of the drip tube, during the predetermined time period; and, generate and transmit an empty bag alarm signal.

26. An optical imaging system for use with an infusion tube having a drip chamber and an output tube, wherein the drip chamber includes a first portion with a drip tube, a second portion with an exit port, and a third portion located between the first and second portions, the optical imaging system comprising:

an illumination system with at least one light source for emitting first light;

an optical system for:

receiving the first light transmitted by the output tube or the second portion; and, transmitting first data characterizing the received first light;

a memory element configured for storing computer executable instructions; and, at least one processor configured for executing the computer executable instructions to:

detect, using the first data, an air bubble in the output tube or the second portion;

determine a volume of the detected air bubble;

identify a peripheral edge shape of a drop pendant from an end of the drip tube for detecting the air bubble;

determine a volume of the drop pendant based on outer surface information of the drop having three dimensional coordinates, wherein the volume of the drop is determined based on at least one of:

a boundary-constrained image of the drop having pixel data representing actual entire outer left and right boundaries of the drop, and a fit-constrained image of the drop representing an entire outer boundary of the drop using a fitting algorithm based on the peripheral edge shape of the drop, wherein:

the at least one light source is configured for emitting third light;

the optical system is configured for:

receiving the third light transmitted by a third portion of the drip chamber; and, transmitting, to the at least one processor, third data characterizing the received third light; and, the at least one processor configured for executing the computer executable instructions to:

create an image of the third portion of the drip chamber;

determine, using the image:

an absence of fluid in the third portion of the drip chamber; or, a fluid level in the third portion below a predetermined level; and, generate and transmit an empty bag alarm or the air alarm signal.

* * * * *